(12) United States Patent
Borns

(10) Patent No.: US 9,040,276 B2
(45) Date of Patent: May 26, 2015

(54) DNA BINDING PROTEIN-POLYMERASE CHIMERAS

(75) Inventor: Michael Borns, Escondido, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1314 days.

(21) Appl. No.: 11/488,535

(22) Filed: Jul. 17, 2006

(65) Prior Publication Data

US 2007/0141591 A1    Jun. 21, 2007

Related U.S. Application Data

(60) Provisional application No. 60/699,937, filed on Jul. 15, 2005.

(51) Int. Cl.
*C12N 9/12* (2006.01)

(52) U.S. Cl.
CPC .......... *C12N 9/1252* (2013.01); *C07K 2319/80* (2013.01)

(58) Field of Classification Search
None
See application file for complete search history.

(56) References Cited

FOREIGN PATENT DOCUMENTS

| WO | 01/92501 | 12/2001 |
|---|---|---|
| WO | 0192501 A1 | 12/2001 |
| WO | 2004/011605 | 2/2004 |
| WO | 2004037979 A2 | 5/2004 |
| WO | 2004/058942 | 7/2004 |
| WO | 2004087868 A2 | 10/2004 |
| WO | 2006/074233 | 7/2006 |

OTHER PUBLICATIONS

Wang et al., Nucleic Acids Research, vol. 32, pp. 1197-1207, 2004.*
Ngo et al. in The Protein Folding Problem and Tertiary Structure Prediction, 1994, Merz et al. (ed.), Birkhauser, Boston, MA, pp. 433 and 492-495.*
Chen et al., "Evolutionary Conservation and DNA Binding Properties of the Ssh7 Proteins from Sulfolobus Shibatae," Sicence in China, Series C, Life Sciences/Chinese Academy of Sciences (Dec. 2002):45(6):583-592.
McAfee et al., "Gene Cloning, Expression, and Characterization of the Sac7 Proteins from the Hyperthermophile Sulfolobus acidocaldarius," Biochemistry, American Chemical Society (Jan. 1, 1995):34(31):10063-10077.
Extended European Search Report for EP Application No. 06787626.8.
International Search Report for Application No. PCT/US2006/027739.

* cited by examiner

*Primary Examiner* — Richard Hutson

(57) ABSTRACT

The invention relates to compositions and methods directed to chimeric DNA polymerases, which comprise a mutated DNA binding polypeptide domain and a mutated or wild-type DNA polymerase polypeptide domain.

19 Claims, 3 Drawing Sheets

```
Sso7d/SsoP2/Ssh7A:  ATVKFKYKGEEKEVDISKIKKVWRVGKMISFTYDEGGGKTGRGAVSEKDAPKELLQMLEKQKK---------------  (SEQ ID NO:2)
Ssh7b:              VTVKFKYKGEEKEVDTSKIKKVWRVGKMISFTYDEGGGKTGRGAVSEKDAPKELLQMLEKQKK---------------  (SEQ ID NO:8)
RiboP3/SsoRNase:    ATVKFKYKGEEKQVDISKIKKVWRVGKMISFTYDEGGGKTGRGAVSEKDAPKELLQMMPETGKYFRHKLPDDYPI   (SEQ ID NO:9)
Sto7e:              VTVKFKYKGEEKEVDISKIKKVWRVGKMISFTYDDN-GKTGRGAVSEKDAPKELLQMLEKSGKK--------------  (SEQ ID NO:10)
Sac7d:              VKVKFKYKGEEKEVDTSKIKKVWRVGKMVSFTYDDN-GKTGRGAVSEKDAPKELLDMLARAEREKK------------  (SEQ ID NO:12)
Sac7e:              AKVRFKYKGEEKEVDTSKIKKVWRVGKMVSFTYDDN-GKTGRGAVSEKDAPKELMDMLARAEKKK-------------  (SEQ ID NO:14)
Sac7a:              VKVKFKYKGEEKEVDTSKIKKVWRVGKMVSFTYDDN-GKTGRGAVSEKDAPKELLDMLARAE----------------  (SEQ ID NO:16)
``` underline: positions in Sso7d where natural variation occurs

FIGURE 1

| | # | Mutation | Negatively effected chimera | No effect on chimera |
|---|---|---|---|---|
| N - terminus | 1 | A1V | X | |
| | 2 | T2K | X | |
| | 3 | T2S | X | |
| | 4 | K4R | X | |
| | 5 | E13Q | | X |
| | 6 | I16T | | X |
| | 7 | W23F | X | |
| | 8 | I29V | X | |
| | 9 | I29L | X | |
| | 10 | I29A | X | |
| | 11 | T32S | X | |
| | 12 | E35D | X | |
| | 13 | G37A | X | |
| | 14 | T40S | | X |
| | 15 | G41A | | X |
| | 16 | V45L | | X |
| | 17 | L55V | | X |
| | 18 | Q56D | | X |
| | 19 | Q61E | | X |
| C - terminus | 20 | K63R | | X |

Mutations made in the *Sso7d* subunit of the *Pfu* DNA polymerase chimera.

FIGURE 2

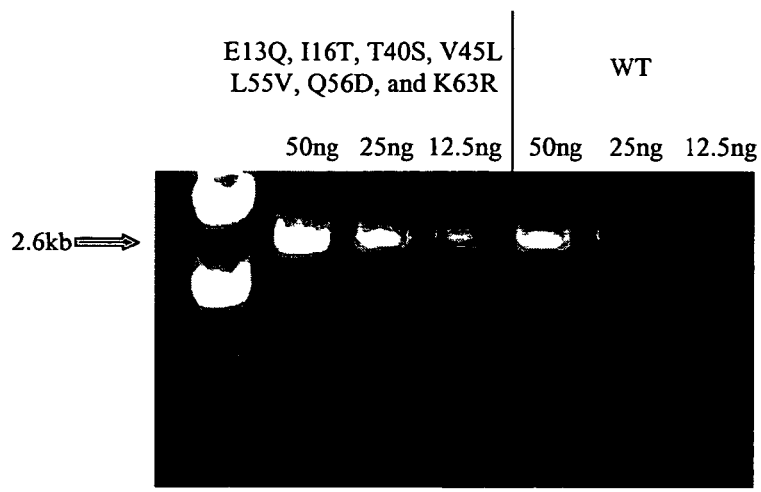
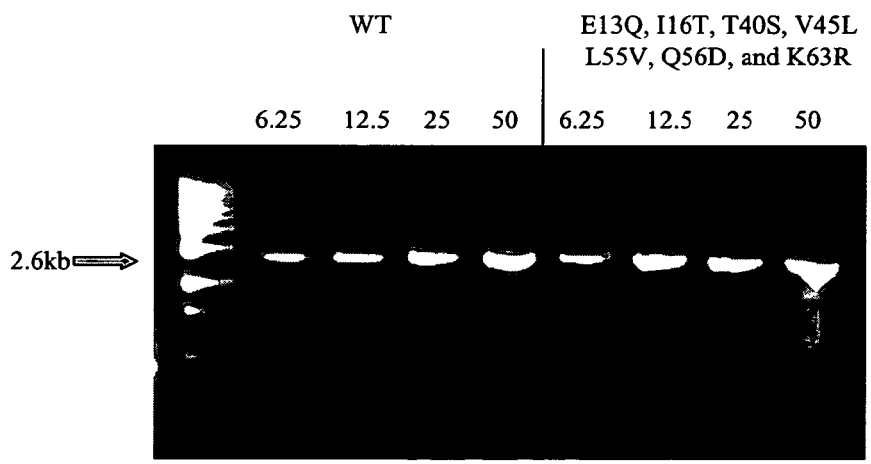
2.6kb human alpha 1 antitrypsin using the pfu chimera with wt Sso7d and the final pfu chimera with the 7 mutant Sso7d (E13Q, I16T, T40S, V45L, L55V, Q56D, and K63R).
FIGURE 3

SEQUENCE LISTING

<160> NUMBER OF SEQ ID NOS: 22

<210> SEQ ID NO 1
<211> LENGTH: 192
<212> TYPE: DNA
<213> ORGANISM: Sulfolobus solfataricus

<400> SEQUENCE: 1

```
gcaacagtaa agttcaagta caagggagaa gagaaggaag tagatataag taagataaag      60
aaggtatgga gagtaggcaa aatgataagt ttcacctatg atgagggtgg aggaaagact     120
ggtagaggag ctgtaagcga gaaagacgct ccaaaagaac tactacaaat gttagaaaag     180
caaaagaaat aa                                                         192
```

<210> SEQ ID NO 2
<211> LENGTH: 63
<212> TYPE: PRT
<213> ORGANISM: Sulfolobus solfataricus

<400> SEQUENCE: 2

```
Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60
```

<210> SEQ ID NO 3
<211> LENGTH: 192
<212> TYPE: DNA
<213> ORGANISM: Artificial
<220> FEATURE:
<223> OTHER INFORMATION: Mutated SSO7D

<400> SEQUENCE: 3

```
gcaacagtaa agttcaagta caagggagaa gagaagcagg tagataccag taagataaag      60
aaggtatgga gagtaggcaa aatgataagt ttcacctatg atgagggtgg aggaaagagt     120
ggtagaggag ctctaagcga gaaagacgct ccaaaagaac tagtagacat gttagaaaag     180
caaaagagat aa                                                         192
```

<210> SEQ ID NO 4
<211> LENGTH: 63
<212> TYPE: PRT
<213> ORGANISM: Artificial
<220> FEATURE:

<223> OTHER INFORMATION: Mutated SSO7D

<400> SEQUENCE: 4

| Ala | Thr | Val | Lys | Phe | Lys | Tyr | Lys | Gly | Glu | Glu | Lys | Gln | Val | Asp | Thr |
|---|---|---|---|---|---|---|---|---|---|---|---|---|---|---|---|
| 1 | | | | 5 | | | | | 10 | | | | | 15 | |

| Ser | Lys | Ile | Lys | Lys | Val | Trp | Arg | Val | Gly | Lys | Met | Ile | Ser | Phe | Thr |
|---|---|---|---|---|---|---|---|---|---|---|---|---|---|---|---|
| | | | 20 | | | | | 25 | | | | | 30 | | |

| Tyr | Asp | Glu | Gly | Gly | Gly | Lys | Ser | Gly | Arg | Gly | Ala | Leu | Ser | Glu | Lys |
|---|---|---|---|---|---|---|---|---|---|---|---|---|---|---|---|
| | | | 35 | | | | | 40 | | | | 45 | | | |

| Asp | Ala | Pro | Lys | Glu | Leu | Val | Asp | Met | Leu | Glu | Lys | Gln | Lys | Arg |
|---|---|---|---|---|---|---|---|---|---|---|---|---|---|---|
| | 50 | | | | | 55 | | | | | 60 | | | |

<210> SEQ ID NO 5
<211> LENGTH: 192
<212> TYPE: DNA
<213> ORGANISM: Artificial
<220> FEATURE:
<223> OTHER INFORMATION: Mutated SSO7D

<400> SEQUENCE: 5

```
gcaacagtaa agttcaagta caagggagaa gagaagcagg tagataccag taagataaag      60
aaggtatgga gagtaggcaa atgataagt ttcacctatg atgagggtgg aggaaagagt      120
ggtagaggag ctctaagcga gaaagacgct ccaaaagaac tagtagacat gttagaaaag     180
gaaaagagat aa                                                          192
```

<210> SEQ ID NO 6
<211> LENGTH: 63
<212> TYPE: PRT
<213> ORGANISM: Artificial
<220> FEATURE:
<223> OTHER INFORMATION: Mutated SSO7D

<400> SEQUENCE: 6

| Ala | Thr | Val | Lys | Phe | Lys | Tyr | Lys | Gly | Glu | Glu | Lys | Gln | Val | Asp | Thr |
|---|---|---|---|---|---|---|---|---|---|---|---|---|---|---|---|
| 1 | | | | 5 | | | | | 10 | | | | | 15 | |

| Ser | Lys | Ile | Lys | Lys | Val | Trp | Arg | Val | Gly | Lys | Met | Ile | Ser | Phe | Thr |
|---|---|---|---|---|---|---|---|---|---|---|---|---|---|---|---|
| | | | 20 | | | | | 25 | | | | | 30 | | |

| Tyr | Asp | Glu | Gly | Gly | Gly | Lys | Ser | Ala | Arg | Gly | Ala | Leu | Ser | Glu | Lys |
|---|---|---|---|---|---|---|---|---|---|---|---|---|---|---|---|
| | | | 35 | | | | | 40 | | | | 45 | | | |

| Asp | Ala | Pro | Lys | Glu | Leu | Val | Asp | Met | Leu | Glu | Lys | Glu | Lys | Arg |
|---|---|---|---|---|---|---|---|---|---|---|---|---|---|---|
| | 50 | | | | | 55 | | | | | 60 | | | |

<210> SEQ ID NO 7
<211> LENGTH: 192
<212> TYPE: DNA
<213> ORGANISM: Sulfolobus shibatae

<400> SEQUENCE: 7

```
gtaacagtaa agttcaagta caagggagaa gagaaggaag tagacacaag taagataaag      60
aaggtatgga gagttggcaa gatgataagc ttcacctatg acgagggtgg aggaaagacc      120
ggtagaggag cagtaagcga gaaagacgct ccaaaagagc tattacaaat gttagagaaa     180
caaaagaaat aa                                                          192
```

<210> SEQ ID NO 8
<211> LENGTH: 63
<212> TYPE: PRT
<213> ORGANISM: Sulfolobus shibatae

<400> SEQUENCE: 8

```
Val Thr Val Lys Phe Lys Tyr Lys Gly Glu Glu Lys Glu Val Asp Thr
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 9
<211> LENGTH: 75
<212> TYPE: PRT
<213> ORGANISM: Sulfolobus solfataricus

<400> SEQUENCE: 9

Ala Thr Val Lys Phe Lys Tyr Lys Gly Glu Glu Lys Gln Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Met Pro Glu Thr Gly Lys Tyr
    50                  55                  60

Phe Arg His Lys Leu Pro Asp Asp Tyr Pro Ile
65                  70                  75

<210> SEQ ID NO 10
<211> LENGTH: 63
<212> TYPE: PRT
<213> ORGANISM: Sulfolobus sp.

<400> SEQUENCE: 10

Val Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Asp Asn Gly Lys Thr Gly Arg Gly Ala Val Ser Glu Lys Asp
        35                  40                  45

Ala Pro Lys Glu Leu Leu Gln Met Leu Glu Lys Ser Gly Lys Lys
    50                  55                  60

<210> SEQ ID NO 11
<211> LENGTH: 198
<212> TYPE: DNA
<213> ORGANISM: Sulfolobus acidocaldarius

<400> SEQUENCE: 11
gtgaaggtaa agttcaagta taagggtgaa gagaaagaag tagacacttc aaagataaag      60
aaggtttgga gagtaggcaa aatggtgtcc tttacctatg acgacaatgg taagacaggt     120
agaggagctg taagcgagaa agatgctcca aaagaattat tagacatgtt agcaagagca     180
gaaagagaga agaaataa                                                   198

<210> SEQ ID NO 12
<211> LENGTH: 65
<212> TYPE: PRT
<213> ORGANISM: Sulfolobus acidocaldarius

<400> SEQUENCE: 12
```

```
Val Lys Val Lys Phe Lys Tyr Lys Gly Glu Glu Lys Glu Val Asp Thr
1               5                   10                  15

Ser Lys Ile Lys Lys Val Trp Arg Val Gly Lys Met Val Ser Phe Thr
            20                  25                  30

Tyr Asp Asp Asn Gly Lys Thr Gly Arg Gly Ala Val Ser Glu Lys Asp
                35                  40                  45

Ala Pro Lys Glu Leu Leu Asp Met Leu Ala Arg Ala Glu Arg Glu Lys
    50                  55                  60

Lys
65

<210> SEQ ID NO 13
<211> LENGTH: 198
<212> TYPE: DNA
<213> ORGANISM: Sulfolobus acidocaldarius

<400> SEQUENCE: 13
atggcaaaag tcaggtttaa gtataagggt gaagagaaag aagtagacac ttcaaagata      60
aagaaggtct ggagagttgg caaaatggtg tcctttacct atgacgacaa tggtaagaca     120
ggtagaggag ctgtaagcga aaaagacgct ccaaaagaac taatggacat gttagcaaga     180
gcagaaaaga agaagtaa                                                   198

<210> SEQ ID NO 14
<211> LENGTH: 64
<212> TYPE: PRT
<213> ORGANISM: Sulfolobus acidocaldarius

<400> SEQUENCE: 14

Ala Lys Val Arg Phe Lys Tyr Lys Gly Glu Glu Lys Glu Val Asp Thr
1               5                   10                  15

Ser Lys Ile Lys Lys Val Trp Arg Val Gly Lys Met Val Ser Phe Thr
            20                  25                  30

Tyr Asp Asp Asn Gly Lys Thr Gly Arg Gly Ala Val Ser Glu Lys Asp
                35                  40                  45

Ala Pro Lys Glu Leu Met Asp Met Leu Ala Arg Ala Glu Lys Lys Lys
    50                  55                  60

<210> SEQ ID NO 15
<211> LENGTH: 183
<212> TYPE: DNA
<213> ORGANISM: Sulfolobus acidocaldarius

<400> SEQUENCE: 15
gtgaaggtaa agttcaagta taagggtgaa gagaaagaag tagacacttc aaagataaag      60
aaggtttgga gagtaggcaa aatggtgtcc tttacctatg acgacaatgg taagacaggt     120
agaggagctg taagcgagaa agatgctcca aaagaattat tagacatgtt agcaagagca     180
gaa                                                                   183

<210> SEQ ID NO 16
<211> LENGTH: 61
<212> TYPE: PRT
<213> ORGANISM: Sulfolobus acidocaldarius

<400> SEQUENCE: 16

Val Lys Val Lys Phe Lys Tyr Lys Gly Glu Glu Lys Glu Val Asp Thr
1               5                   10                  15
```

```
Ser Lys Ile Lys Lys Val Trp Arg Val Gly Lys Met Val Ser Phe Thr
         20                  25                  30

Tyr Asp Asp Asn Gly Lys Thr Gly Arg Gly Ala Val Ser Glu Lys Asp
         35                  40                  45

Ala Pro Lys Glu Leu Leu Asp Met Leu Ala Arg Ala Glu
         50                  55                  60

<210> SEQ ID NO 17
<211> LENGTH: 2325
<212> TYPE: DNA
<213> ORGANISM: Pyrococcus furiosus

<400> SEQUENCE: 17
atgattttag atgtggatta cataactgaa gaaggaaaac ctgttattag gctattcaaa      60
aaagagaacg gaaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt      240 accgtgtgga aactttattt ggaacatccc caagatgttc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gatatagaaa ccctctatca cgaaggagaa gagtttggaa aaggcccaat tataatgatt     480
agttatgcag atgaaaatga agcaaaggtg attacttgga aaaacataga tcttccatac     540
gttgaggttg tatcaagcga gagagagatg ataaagagat tctctcagga tatcagggag     600
aaggatcctg acattatagt tacttataat ggagactcat tcgacttccc atatttagcg     660 aaaaggcag aaaacttgg gattaaatta accattggaa gagatggaag cgagcccaag      720
atgcagagaa taggcgatat gacggctgta gaagtcaagg gaagaataca tttcgacttg     780
tatcatgtaa taacaaggac aataaatctc ccaacataca cactagaggc tgtatatgaa     840
gcaatttttg gaaagccaaa ggagaaggta tacgccgacg atagcaaa agcctgggaa       900 agtggagaga acctttgagag agttgccaaa tactcgatgg aagatgcaaa ggcaacttat     960
gaactcggga agaattcct tccaatggaa attcagcttt caagattagt tggacaacct    1020
ttatgggatg tttcaaggtc aagcacaggg aaccttgtag agtggttctt acttaggaaa    1080
gcctacgaaa gaaacgaagt agctccaaac aagccaagtg aagaggagta tcaaagaagg    1140
ctcagggaga gctacacagg tggattcgtt aaagagccag aaaagggggtt gtgggaaaac    1200 atagtatacc tagattttag agccctatat ccctcgatta taattaccca caatgtttct    1260
cccgatactc taaatcttga gggatgcaag aactatgata tcgctcctca gtaggccac     1320 aagttctgca aggacatccc tggttttata ccaagtctct gggacatttt gttagggaa     1380 agacaaaaga ttaagacaaa atgaaggaa actcaagatc ctatagaaaa aatactcctt    1440
gactatagac aaaaagcgat aaaactctta gcaaattctt tctacggata ttatggctat    1500
gcaaaagcaa gatggtactg taaggagtgt gctgagagcg ttactgcctg gggaagaaag    1560
tacatcgagt tagtatggaa ggagctcgaa gaaaagtttg gatttaaagt cctctacatt    1620
gacactgatg gtctctatgc aactatccca ggaggagaaa gtgaggaaat aaagaaaaag    1680
gctctagaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
```

```
aaagaaactc aagctagagt tttggagaca atactaaaac acggagatgt tgaagaagct   1920
gtgagaatag taaagaagt aatacaaaag cttgccaatt atgaaattcc accagagaag    1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca ttgagaacca ggttcttcca   2220
gcggtactta ggatattgga gggatttgga tacagaaagg aagacctcag ataccaaaag   2280
acaagacaag tcggcctaac ttcctggctt aacattaaaa aatcc                   2325
```

<210> SEQ ID NO 18
<211> LENGTH: 775
<212> TYPE: PRT
<213> ORGANISM: Pyrococcus furiosus

<400> SEQUENCE: 18

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
```

```
            290                 295                 300
Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
            450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
            690                 695                 700

Leu Arg Gly Asp Gly Pro Ile Ser Asn Arg Ala Ile Leu Ala Glu Glu
705                 710                 715                 720
```

```
Tyr Asp Pro Lys Lys His Lys Tyr Asp Ala Glu Tyr Ile Glu Asn
            725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
            755                 760                 765
Trp Leu Asn Ile Lys Lys Ser
    770                 775

<210> SEQ ID NO 19
<211> LENGTH: 2538
<212> TYPE: DNA
<213> ORGANISM: Artificial
<220> FEATURE:
<223> OTHER INFORMATION: Pfu Polymerase SSO7D mutated chimera

<400> SEQUENCE: 19
```

| | | |
|---|---|---|
| atgatttag atgtggatta cataactgaa gaaggaaaac ctgttattag gctattcaaa | 60 |
| aaagagaacg gaaaatttaa gatagagcat gatagaactt ttagaccata catttacgct | 120 |
| cttctcaggg atgattcaaa gattgaagaa gttaagaaaa taacggggga aaggcatgga | 180 |
| aagattgtga gaattgttga tgtagagaag gttgagaaaa agtttctcgg caagcctatt | 240 |
| accgtgtgga actttatttt ggaacatccc caagatgttc ccactattag agaaaaagtt | 300 |
| agagaacatc cagcagttgt ggacatcttc gaatacgata ttccatttgc aaagagatac | 360 |
| ctcatcgaca aggcctaat accaatggag ggggaagaag agctaaagat tcttgccttc | 420 |
| gatatagaaa ccctctatca cgaaggagaa gagtttggaa aaggcccaat tataatgatt | 480 |
| agttatgcag atgaaaatga agcaaaggtg attacttgga aaaacataga tcttccatac | 540 |
| gttgaggttg tatcaagcga gagagagatg ataaagagat tctctcagga tatcagggag | 600 |
| aaggatcctg acattatagt tacttataat ggagactcat tcgacttccc atatttagcg | 660 |
| aaaagggcag aaaacttgg gattaaatta accattggaa gagatggaag cgagcccaag | 720 |
| atgcagagaa taggcgatat gacggctgta gaagtcaagg aagaatacat tttcgacttg | 780 |
| tatcatgtaa taacaaggac aataaatctc ccaacataca cactgagggc tgtatatgaa | 840 |
| gcaattttg gaaagccaaa ggagaaggta tacgccgacg agatagcaaa agcctgggaa | 900 |
| agtggagaga accttgagag agttgccaaa tactcgatgg aagatgcaaa ggcaacttat | 960 |
| gaactcggga agaattcct tccaatggaa attcagcttt caagattagt tggacaacct | 1020 |
| ttatgggatg tttcaaggtc aagcacaggg aaccttgtag agtggttctt acttaggaaa | 1080 |
| gcctacgaaa gaaacgaagt agctccaaac aagccaagtg aagaggagta tcaaagaagg | 1140 |
| ctcagggaga gctacacagg tggattcgtt aagagccag aaaagggggtt gtgggaaaac | 1200 |
| atagtatacc tagattttag agccctatat ccctcgatta aattaccca caatgtttct | 1260 |
| cccgatactc taaatcttga gggatgcaag aactatgata tcgctcctca gtaggccac | 1320 |
| aagttctgca aggacatccc tggttttata ccaagtctct tgggacattt gttagaggaa | 1380 |
| agacaaaaga ttaagacaaa aatgaaggaa actcaagatc ctatagaaaa aatactcctt | 1440 |
| gactatagac aaaaagcgat aaaactctta gcaaattctt tctacggata ttatggctat | 1500 |
| gcaaaagcaa gatggtactg taaggagtgt gctgagagcg ttactgcctg ggaagaaag | 1560 |
| tacatcgagt tagtatggaa ggagctcgaa gaaaagtttg gatttaaagt cctctacatt | 1620 |
| gacactgatg gtctctatgc aactatccca ggaggagaaa gtgaggaaat aaagaaaaag | 1680 |

-continued

```
gctctagaat ttgtaaaata cataaattca aagctccctg gactgctaga gcttgaatat    1740
gaagggtttt ataagagggg attcttcgtt acgaagaaga ggtatgcagt aatagatgaa    1800
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatccggtac cggcggtggc    2340
ggtgcaacag taaagttcaa gtacaaggga agagaagc aggtagatac cagtaagata    2400
aagaaggtat ggagagtagg caaaatgata agtttcacct atgatgaggg tggaggaaag    2460
agtggtagag gagctctaag cgagaaagac gctccaaaag aactagtaga catgttagaa    2520
aagcaaaaga gataatag                                                  2538
```

<210> SEQ ID NO 20
<211> LENGTH: 844
<212> TYPE: PRT
<213> ORGANISM: Artificial
<220> FEATURE:
<223> OTHER INFORMATION: Pfu polymerase, SSO7D mutated chimera

<400> SEQUENCE: 20

| Met | Ile | Leu | Asp | Val | Asp | Tyr | Ile | Thr | Glu | Glu | Gly | Lys | Pro | Val | Ile |
|---|---|---|---|---|---|---|---|---|---|---|---|---|---|---|---|
| 1 | | | | 5 | | | | | 10 | | | | | 15 | |

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Lys Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

```
Tyr Asn Gly Asp Ser Phe Asp Phe Pro Tyr Leu Ala Lys Arg Ala Glu
    210             215                 220

Lys Leu Gly Ile Lys Leu Thr Ile Gly Arg Asp Gly Ser Glu Pro Lys
225             230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Thr Gly Asn Leu
                340                 345                 350

Val Glu Trp Phe Leu Leu Arg Lys Ala Tyr Glu Arg Asn Glu Val Ala
            355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
                595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
```

```
                    625                 630                 635                 640
     Val Arg Ile Val Lys Glu Val Ile Gln Lys Leu Ala Asn Tyr Glu Ile
                        645                 650                 655

Pro Pro Glu Lys Leu Ala Ile Tyr Glu Gln Ile Thr Arg Pro Leu His
                        660                 665                 670

Glu Tyr Lys Ala Ile Gly Pro His Val Ala Val Ala Lys Lys Leu Ala
                        675                 680                 685

Ala Lys Gly Val Lys Ile Lys Pro Gly Met Val Ile Gly Tyr Ile Val
                        690                 695                 700

Leu Arg Gly Asp Gly Pro Ile Ser Asn Arg Ala Ile Leu Ala Glu Glu
     705                 710                 715                 720

Tyr Asp Pro Lys Lys His Lys Tyr Asp Ala Glu Tyr Tyr Ile Glu Asn
                        725                 730                 735

Gln Val Leu Pro Ala Val Leu Arg Ile Leu Glu Gly Phe Gly Tyr Arg
                        740                 745                 750

Lys Glu Asp Leu Arg Tyr Gln Lys Thr Arg Gln Val Gly Leu Thr Ser
                        755                 760                 765

Trp Leu Asn Ile Lys Lys Ser Gly Thr Gly Gly Gly Gly Ala Thr Val
                        770                 775                 780

Lys Phe Lys Tyr Lys Gly Glu Glu Lys Gln Val Asp Thr Ser Lys Ile
     785                 790                 795                 800

Lys Lys Val Trp Arg Val Gly Lys Met Ile Ser Phe Thr Tyr Asp Glu
                        805                 810                 815

Gly Gly Gly Lys Ser Gly Arg Gly Ala Leu Ser Glu Lys Asp Ala Pro
                        820                 825                 830

Lys Glu Leu Val Asp Met Leu Glu Lys Gln Lys Arg
                        835                 840
```

<210> SEQ ID NO 21
<211> LENGTH: 2538
<212> TYPE: DNA
<213> ORGANISM: Artificial
<220> FEATURE:
<223> OTHER INFORMATION: Non-mutated Pfu polymerase-SSO7D chimera

<400> SEQUENCE: 21

```
atgattttag atgtggatta cataactgaa gaaggaaaac ctgttattag gctattcaaa      60
aaagagaacg aaaatttaa gatagagcat gatagaactt ttagaccata catttacgct     120
cttctcaggg atgattcaaa gattgaagaa gttaagaaaa taacggggga aaggcatgga     180
aagattgtga gaattgttga tgtagagaag gttgagaaaa gtttctcgg caagcctatt     240
accgtgtgga acttttattt ggaacatccc caagatgttc ccactattag agaaaaagtt     300
agagaacatc cagcagttgt ggacatcttc gaatacgata ttccatttgc aaagagatac     360
ctcatcgaca aaggcctaat accaatggag ggggaagaag agctaaagat tcttgccttc     420
gatatagaaa ccctctatca cgaaggagaa gagtttggaa aaggccaat tataatgatt     480
agttatgcag atgaaaatga agcaaaggtg attacttgga aaaacataga tcttccatac     540
gttgaggttg tatcaagcga gagagagatg ataaagagat ttctcaggat tatcagggag     600
aaggatcctg acattatagt tacttataat ggagactcat tcgacttccc atatttagcg     660
aaaaggcag aaaaacttgg gattaaaatta accattggaa gagatggaag cgagcccaag     720
atgcagagaa taggcgatat gacggctgta gaagtcaagg aagaatacat ttcgacttg     780
tatcatgtaa taacaaggac aataaaatctc ccaacataca cactagaggc tgtatatgaa     840
```

-continued

```
gcaattttg gaaagccaaa ggagaaggta tacgccgacg agatagcaaa agcctgggaa      900
agtggagaga accttgagag agttgccaaa tactcgatgg aagatgcaaa ggcaacttat      960
gaactcggga agaattcct tccaatggaa attcagcttt caagattagt tggacaacct     1020
ttatgggatt tttcaaggtc aagcacaggg aaccttgtag agtggttctt acttaggaaa     1080
gcctacgaaa gaaacgaagt agctccaaac aagccaagtg aagaggagta tcaaagaagg     1140
ctcagggaga gctacacagg tggattcgtt aaagagccag aaaagggggtt gtgggaaaac     1200
atagtatacc tagattttag agccctatat ccctcgatta taattaccca caatgtttct     1260
cccgatactc taaatcttga gggatgcaag aactatgata tcgctcctca agtaggccac     1320
aagttctgca aggacatccc tggttttata ccaagtctct tgggacattt gttagaggaa     1380
agacaaaaga ttaagacaaa aatgaaggaa actcaagatc ctatagaaaa aatactcctt     1440
gactatagac aaaaagcgat aaaactctta gcaaattctt tctacggata ttatggctat     1500
gcaaaagcaa gatggtactg taaggagtgt gctgagagcg ttactgcctg gggaagaaag     1560
tacatcgagt tagtatggaa ggagctcgaa gaaaagtttg gatttaaagt cctctacatt     1620
gacactgatg gtctctatgc aactatccca ggaggagaaa gtgaggaaat aaagaaaaag     1680
gctctagaat ttgtaaaata cataaaattca agctccctg gactgctaga gcttgaatat     1740
gaagggtttt ataagagggg attcttcgtt acgaagaaga ggtatgcagt aatagatgaa     1800
gaaggaaaag tcattactcg tggtttagag atagttagga gagattggag tgaaattgca     1860
aaagaaactc aagctagagt tttggagaca atactaaaac acggagatgt tgaagaagct     1920
gtgagaatag taaagaagt aatacaaaag cttgccaatt atgaaattcc accagagaag     1980
ctcgcaatat atgagcagat aacaagacca ttacatgagt ataaggcgat aggtcctcac     2040
gtagctgttg caaagaaact agctgctaaa ggagttaaaa taaagccagg aatggtaatt     2100
ggatacatag tacttagagg cgatggtcca attagcaata gggcaattct agctgaggaa     2160
tacgatccca aaagcacaa gtatgacgca gaatattaca ttgagaacca ggttcttcca     2220
gcggtactta ggatattgga gggatttgga tacagaaagg aagacctcag ataccaaaag     2280
acaagacaag tcggcctaac ttcctggctt aacattaaaa aatccggtac cggcggtggc     2340
ggtgcaacag taaagttcaa gtacaaggga gaagagaagg aagtagatat aagtaagata     2400
aagaaggtat ggagagtagg caaaatgata agtttcacct atgatgaggg tggaggaaag     2460
actggtagag gagctgtaag cgagaaagac gctccaaaag aactactaca aatgttagaa     2520
aagcaaaaga ataatag                                                  2538
```

<210> SEQ ID NO 22
<211> LENGTH: 844
<212> TYPE: PRT
<213> ORGANISM: Artificial
<220> FEATURE:
<223> OTHER INFORMATION: Non-mutated Pfu polymerase-SSO7D chimera

<400> SEQUENCE: 22

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60
```

```
Ile Val Asp Val Glu Lys Val Glu Lys Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480
```

```
Asp Tyr Arg Gln Lys Ala Ile Lys Leu Leu Ala Asn Ser Phe Tyr Gly
            485                 490                 495

Tyr Tyr Gly Tyr Ala Lys Ala Arg Trp Tyr Cys Lys Glu Cys Ala Glu
        500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840
```

DNA BINDING PROTEIN-POLYMERASE CHIMERAS

RELATED APPLICATION

This application claims priority under 35 U.S.C. 119(e) to U.S. Provisional Application Ser. No. 60/699,937 filed Jul. 15, 2005, the entirety of which is incorporated herein by reference.

BACKGROUND

One approach to modifying the property of a DNA polymerase is to generate chimeric DNA polymerases in which one or more protein domains having the requisite activity are combined with a DNA polymerase. A DNA polymerase has been fused in frame to the helix-hairpin-helix DNA binding motifs from DNA topoisomerase V and shown to increase processivity, salt resistance and thermostability of the chimeric DNA polymerase as described in Pavlov et al., 2002, Proc. Natl. Acad. Sci USA, 99:13510-13515. Also, fusion of the sequence non-specific DNA binding protein of wild-type Sso7d or Sac7d from *Sulfolobus sulfataricus* to a DNA polymerase, such as Pfu or Taq DNA polymerase, was shown to greatly increase the processivity of these DNA polymerases as disclosed in WO 01/92501 A1 and US2004/0081963 A1, which are hereby incorporated by reference in their entirety.

SUMMARY OF THE INVENTION

The invention relates to chimeric DNA polymerases, which comprise a first domain and a second domain. The first domain includes a mutated or wild-type DNA polymerase polypeptide and the second domain includes a mutated DNA binding polypeptide. The DNA binding domain may include a complete DNA binding polypeptide sequence, or a fragment thereof. Similarly the DNA polymerase domain may include a complete DNA polymerase polypeptide sequence, or a fragment thereof.

In a first aspect, the invention relates to a chimeric DNA polymerase having a DNA binding domain and a DNA polymerase domain. The DNA binding domain of the chimeric DNA polymerase is mutated at one or more amino acids selected from the group consisting of 13, 16, 40, 41, 45, 55, 56, 61 or 63 of SEQ ID NO:2, or at a corresponding position in an Sso7d-like protein.

In a related aspect, the invention relates to a chimeric DNA polymerase having a DNA binding domain and a DNA polymerase domain. The DNA binding domain of the chimeric DNA polymerase is mutated at amino acid positions 13, 16, 40, 45, 55, 56, and 63 of SEQ ID NO:2, or at a corresponding position in an Sso7d-like protein.

In another aspect, the invention provides a chimeric DNA polymerase having a DNA binding domain and a polymerase domain. In this aspect, the DNA binding domain is mutated at amino acid positions 13, 16, 40, 41, 45, 55, 56, 61 and 63 of SEQ ID NO:2, or in a corresponding position in an Sso7d-like protein.

In yet another aspect, the invention relates to a chimeric DNA polymerase having a DNA binding domain and a DNA polymerase domain. In this aspect, the DNA binding domain comprises the amino acid sequence of SEQ ID NO:4.

In still another aspect of the invention, the invention provides a chimeric DNA polymerase including a DNA binding domain and a polymerase domain, wherein the DNA binding domain comprises the amino acid sequence of SEQ ID NO:6.

In yet another aspect of the invention, the invention provides a chimeric DNA polymerase including a DNA binding domain and a polymerase domain. The DNA polymerase domain comprises a Pfu DNA polymerase polypeptide and the DNA binding domain comprises a mutated Sso7d DNA binding polypeptide.

In yet another aspect of the invention, the invention provides for a chimeric DNA polymerase including a DNA binding domain and a polymerase domain, wherein said chimeric DNA polymerase comprises the amino acid sequence of SEQ ID NO:20.

In another aspect of the invention, the invention provides for a method of synthesizing DNA comprising providing a chimeric DNA polymerase of the invention, and contacting the chimeric DNA polymerase with a nucleic acid template.

In yet another aspect of the invention, the invention provides for a method of producing a chimeric DNA polymerase by expressing a nucleic acid encoding the chimeric DNA polymerases described herein.

In additional aspects of the invention, the invention provides for compositions and kits comprising the chimeric DNA polymerases of the invention. The kits including any one of the compositions described herein above and packaging material therefore. In other aspects, the invention provides for nucleic acids and vectors encoding the chimeric DNA polymerases described herein and host cells transfected with such vectors.

BRIEF DESCRIPTION OF THE DRAWINGS

FIG. 1 depicts a protein sequence alignment between Sso7d and Sso7d-like polypeptides (Ssh7b, RiboP3, Sto7e, Sac7d, Sac7e and Sac7a).

FIG. 2 identifies mutations (column 1) made to the Sso7d domain of a Pfu DNA polymerase chimera. Mutations that negatively effected the chimera are indicated in column 2, while column 3 identifies mutations that did not negatively effect the chimera.

FIG. 3 depicts the results of an amplification reaction and Gel shift assay comparing a chimeric DNA polymerase comprising a wild-type Sso7d polypeptide with a chimeric DNA polymerase comprising a mutated Sso7d polypeptide. The Sso7d polypeptide was mutated to E13Q, I16T, T40S, V45L, L55V, Q56D and K63R.

DETAILED DESCRIPTION

Definitions

A "chimeric DNA polymerase" as defined herein, is a fusion of a first amino acid sequence comprising a wild type or mutant DNA polymerase domain of the invention, joined to a second amino acid sequence comprising a mutant DNA binding domain. A chimeric DNA polymerase according to the invention contains two or more amino acid sequences (for example a sequence encoding a wild type or mutant DNA polymerase domain and a polypeptide that encodes a mutant DNA binding domain) from unrelated proteins, joined to form a new functional protein. In one embodiment, a chimeric DNA polymerase according to the invention comprises a first amino acid sequence derived from a Pfu DNA polymerase and a second amino acid sequence derived from a mutated Sso7d DNA binding protein. The invention encompasses chimeric DNA polymerase wherein the DNA binding domain polypeptide is joined N-terminally or C-terminally to, or is inserted at any internal position of a wild-type or mutant DNA polymerases domain described herein.

"Domain" refers to a unit of a protein or protein complex, comprising a polypeptide subsequence, a complete polypeptide sequence, or a plurality of polypeptide sequences.

As used herein, the phrase "polymerase domain" refers to a protein domain, which catalyzes the polymerization of nucleotides. Polymerase domains include the nucleic acid polymerases described herein and those known in the art.

As used herein, "polymerase" refers to an enzyme that catalyzes the polymerization of nucleotides (i.e., the polymerase activity). Generally, the enzyme will initiate synthesis at the 3'-end of the primer annealed to a polynucleotide template sequence, and will proceed toward the 5' end of the template strand. "DNA polymerase" catalyzes the polymerization of deoxynucleotides. In one embodiment, the DNA polymerase according to the invention is thermostable. In another embodiment, the DNA polymerase according to the invention is an archaeal DNA polymerase.

The nucleic acid polymerases used in the present invention may be mesophilic or thermophilic, and are preferably thermophilic. Mesophilic DNA polymerases include T7 DNA polymerase, T5 DNA polymerase, T4 DNA polymerase, Klenow fragment DNA polymerase, DNA polymerase III and the like. Thermostable DNA polymerases that may be used in the methods of the invention include Taq, Tne, Tma, Pfu, Tfl, Tth, Stoffel fragment, VENT™ and DEEPVENT™ DNA polymerases, KOD, Tgo, JDF3, and mutants, variants and derivatives thereof (U.S. Pat. No. 5,436,149; U.S. Pat. No. 4,889,818; U.S. Pat. Nos. 4,965,18S; 5,079,352; U.S. Pat. No. 5,614,365; U.S. Pat. Nos. 5,374,553; 5,270,179; 5,047,342; 5,512,462; WO 92/06188; WO 92/06200; WO 96/10640; Barnes, W. M., Gene 112:29-35 (1992); Lawyer, F. C., et al., PCR Meth. Appl. 2:275-287 (1993); Flaman, J.-M, et al., Nuc. Acids Res. 22(15):3259-3260 (1994)).

As used herein, "archaeal" DNA polymerase refers to DNA polymerases that belong to either the Family B/pol I-type group (e.g., Pfu, KOD, Pfx, Vent, Deep Vent, Tgo, Pwo) or the pol II group (e.g., *Pyrococcus furiosus* DP1/DP2 2-subunit DNA polymerase). In one embodiment, "archaeal" DNA polymerase refers to thermostable archaeal DNA polymerases (PCR-able) and include, but are not limited to, DNA polymerases isolated from *Pyrococcus* species (furiosus, species GB-D, *woesii, abysii, horikoshii*), *Thermococcus* species (*kodakaraensis* KOD1, *litoralis*, species 9 degrees North-7, species JDF-3, *gorgonarius*), *Pyrodictium occultum*, and *Archaeoglobus fulgidus*. It is estimated that suitable archaea would exhibit maximal growth temperatures of >80-85° C. or optimal growth temperatures of >70-80° C. Appropriate PCR enzymes from the archaeal pol I DNA polymerase group are commercially available, including Pfu (Stratagene), KOD (Toyobo), Pfx (Life Technologies, Inc.), Vent (New England BioLabs), Deep Vent (New England BioLabs), Tgo (Roche), and Pwo (Roche). Additional archaea related to those listed above are described in the following references: Archaea: A Laboratory Manual (Robb, F. T. and Place, A. R., eds.), Cold Spring Harbor Laboratory Press, Cold Spring Harbor, N.Y., 1995.

As used herein, "thermostable" refers to an enzyme which is stable to heat, is heat resistant, and functions at high temperatures, e.g., 50 to 100° C., as compared, for example, to a non-thermostable form of an enzyme with a similar activity. For example, a thermostable nucleic acid polymerase derived from thermophilic organisms such as *P. furiosus, M. jannaschii, A. fulgidus* or *P. horikoshii* are more stable and active at elevated temperatures as compared to a nucleic acid polymerase from *E. coli*. A representative thermostable nucleic acid polymerase isolated from *P. furiosus* (Pfu) is described in Lundberg et al., 1991, *Gene,* 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis*, and *Methanothermus fervidus*.

Temperature stable polymerases are preferred in a thermocycling process wherein double stranded nucleic acids are denatured by exposure to a high temperature (about 95° C.) during the PCR cycle.

As used herein, "mutant DNA polymerase" refers to a DNA polymerase, as defined herein, comprising one or more mutations that modulate, as defined herein, one or more activities of the DNA polymerase including, but not limited to, DNA polymerization activity, base analog detection activities, 3'-5' or 5'-3' exonuclease activities, processivity improved nucleotide analog incorporation activity, proofreading, fidelity, efficiency, specificity, thermostability and intrinsic hot start capability or decreased DNA polymerization at room temperature, decreased amplification slippage on templates with tri-nucleotide repeat stretches or homopolymeric stretches, decreased amplification cycles, decreased extension times, reduced sensitivity to inhibitors (e.g., high salt, nucleic acid purification reagents), altered optimal reaction conditions (e.g., pH, KCL) and a decrease in the amount of polymerase needed for the applications described herein.

As used herein, the term "DNA binding domain" refers to nucleic acid and polypeptide mutants and interspecies homologues that comprise one or more mutations in a Sso7d polypeptide or Sso7d-like polypeptide. Sso7d-like polypeptides include Sac7d, Sac7e, Ssh7b, RiboP3, Sto7e and Sac7a. In one embodiment, the DNA binding domain has one or more mutations in an amino acid sequence of SEQ ID NO: 2, 4, 6, 8, 9, 10, 12, 14 and 16. The mutations occur at amino acid positions 13, 16, 40, 41, 45, 55, 56, 61 or 63 of SEQ ID NO:2 and in corresponding amino acid residues of homologues thereof. The term includes both full-length polypeptides and fragments of the polypeptides that have sequence non-specific double-stranded DNA binding activity. DNA binding domains are described in WO01/92501 and U.S. Publication No. 2004/0219558, both of which are herein incorporated in their entirety.

As used herein, "joined" refers to any method known in the art for functionally connecting polypeptide domains, including without limitation recombinant fusion with or without intervening domains, intein-mediated fusion, non-covalent association, and covalent bonding, including disulfide bonding, hydrogen bonding, electrostatic bonding, and conformational bonding.

The term "corresponds to," when used in the context of similarity or homology between protein sequences or domains means that an amino acid at a particular position in a first polypeptide is identical or similar to a corresponding amino acid in a second polypeptide that is in an optimal global sequence alignment with the first polypeptide. An optimal global alignment is achieved using, for example, the Needleman-Wunsch algorithm (Needleman and Wunsch, 1970, J. Mol. Biol. 48:443-453). "Identity" means that an amino acid at a particular position in a first polypeptide is identical to a corresponding amino acid or nucleotide in a second polypeptide that is in an optimal global alignment with the first polypeptide or polynucleotide. In contrast to identity, "similarity" encompasses amino acids that are conservative substitutions. A "conservative" substitution is any substitution that has a positive score in the blosum62 substitution matrix (Hentikoff and Hentikoff, 1992, Proc. Natl. Acad. Sci. USA 89: 10915-10919). Typical conservative substitutions are among Met, Val, Leu and Ile; among Ser and Thr; among the residues Asp, Glu and Asn; among the residues Gln, Lys and Arg; or aromatic residues Phe and Tyr.

An example of the parameters for optimal global sequence alignment using the Needleman-Wunsch alignment algorithm for polypeptide alignment useful to determine "corresponding" sequences or domains are as follows: Substitution matrix: blosum62; Gap scoring function: −A−B*LG, where A=11 (the gap penalty), B=1 (the gap length penalty) and LG is the length of the gap. Using the Needleman-Wunsch algorithm and these parameters, or using other alignment software known in the art, one of skill in the art can readily determine whether a given amino acid, sequence of amino acids, or region of sequence in a given DNA binding protein, e.g., Sso7d (SEQ ID NO:2), "corresponds to" an amino acid, sequence of amino acids or region of sequence in a Sso7d like DNA binding protein, e.g., Ssh7b (SEQ ID NO:8), disclosed herein.

As used herein, the term "template DNA molecule" refers to that strand of a nucleic acid from which a complementary nucleic acid strand is synthesized by a DNA polymerase, for example, in a primer extension reaction.

As used herein, an "amplified product" refers to the double strand polynucleotide population at the end of a PCR amplification reaction. The amplified product contains the original polynucleotide template and polynucleotide synthesized by DNA polymerase using the polynucleotide template during the PCR reaction.

As used herein, the term "primer" refers to a single stranded DNA or RNA molecule that can hybridize to a polynucleotide template and prime enzymatic synthesis of a second polynucleotide strand. A primer useful according to the invention is between 10 to 100 nucleotides in length, preferably 17-50 nucleotides in length and more preferably 17-45 nucleotides in length.

"Complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. For example, a mutant DNA biding domain exhibits a different nucleic acid and amino acid sequence than a wild type DNA binding domain.

As used herein, the term "cell", "cell line" and "cell culture" can be used interchangeably and all such designations include progeny. Thus, the term "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

As used herein, the term "organism transformed with a vector" or "cell transformed with a vector" refers to an organism or cell carrying a recombinant gene construct.

As used herein, the term "recombinant" refers to a polynucleotide or polypeptide that is altered by genetic engineering (i.e., by modification or manipulation of the genetic material encoding that polynucleotide or polypeptide).

DESCRIPTION

The invention relates to chimeric DNA polymerases, which comprise a first domain and a second domain. The first domain includes a mutated or wild-type DNA polymerase polypeptide and the second domain includes a mutated DNA binding polypeptide. In a first aspect, the invention relates to a chimeric DNA polymerase having a DNA binding domain and a DNA polymerase domain. The DNA binding domain of the chimeric DNA polymerase is mutated at one or more amino acids at positions 13, 16, 40, 41, 45, 55, 56, 61 or 63 of Sso7d (SEQ ID NO:2), or at a corresponding position in an Sso7d-like protein. In one embodiment, the one or more mutations in the DNA binding domain include E13Q, I16T, T40S, G41A, V45L, L55V, Q56D, Q61E or K63R of SEQ ID NO:2, or a corresponding mutation in an Sso7d-like protein. The amino acid changes include conservatively modified variants of these described hereinabove. In some embodiments, the DNA binding domain comprises a Sso7d like polypeptide. Sso7d-like polypeptides include Ssh7b (SEQ ID NO: 8), RiboP3 (SEQ ID NO: 9), Sto7e (SEQ ID NO: 10), Sac7d (SEQ ID NO: 12), Sac7e (SEQ ID NO: 14) and Sac7a (SEQ ID NO: 16).

In a related aspect, the invention relates to a chimeric DNA polymerase having a DNA binding domain and a DNA polymerase domain: The DNA binding domain of the chimeric DNA polymerase is mutated at amino acid positions 13, 16, 40, 45, 55, 56, and 63 of SEQ ID NO:2, or at a corresponding position in a Sso7d-like protein. In one embodiment of this aspect, the mutations in the DNA binding domain include E13Q, I16T, T40S, V45L, L55V, Q56D, and K63R of SEQ ID NO:2, or a corresponding mutation in a Sso7d-like protein. The Sso7d-like protein may be RiboP3, Sto7e, Sac7d, Sac7e or Sac7a. In another embodiment, the Sso7d-like protein has an amino acid sequence of SEQ ID NO:8, 9, 12, 12, 14 or 16.

In another aspect, the invention provides a chimeric DNA polymerase including a DNA binding domain and a polymerase domain. In this aspect, the DNA binding domain is mutated at amino acid positions 13, 16, 40, 41, 45, 55, 56, 61 and 63 of SEQ ID NO:2, or in a corresponding position in a Sso7d-like protein. In one embodiment of this aspect, the amino acid changes in the DNA binding domain include E13Q, I16T, T40S, G41A, V45L, L55V, Q61E and K63R of SEQ ID NO:2, or a corresponding change in a Sso7d-like protein. The Sso7d-like protein may be RiboP3, Sto7e, Sac7d, Sac7e or Sac7a. In another embodiment, the Sso7d-like protein has an amino acid sequence of SEQ ID NO:8, 9, 12, 12, 14 or 16.

In yet another aspect, the invention relates to a chimeric DNA polymerase having a DNA binding domain and a DNA polymerase domain. In this aspect, the DNA binding domain comprises the amino acid sequence of SEQ ID NO:4.

In still another aspect of the invention, the invention provides a chimeric DNA polymerase including a DNA binding domain and a polymerase domain, wherein the DNA binding domain comprises the amino acid sequence of SEQ ID NO:6.

In one embodiment of the aspects described herein above, the DNA polymerase domain comprises an archaeal DNA polymerase polypeptide. In a further embodiment, the archaeal DNA polymerase polypeptide is a Pfu DNA polymerase polypeptide. In yet another embodiment, the DNA polymerase polypeptide is a Taq DNA polymerase. In yet another embodiment of the aspects described herein above, the chimeric DNA polymerase domain is at least 95% identical with the amino acid sequence of SEQ ID NO: 18.

In another embodiment, of the aspects described herein, the polymerase domain of the chimeric DNA polymerase of the invention comprises a mutated DNA polymerase. The mutated DNA polymerase may comprise a V93R,K,E,D mutation in Pfu DNA polymerase, which confer uracil insensitivity. In further embodiment, the mutated DNA polymerase has D141A and/or E143A in Pfu DNA polymerase, which eliminates 3'-5' exonuclease activity.

In additional aspects of the invention, the invention provides for compositions and kits comprising the chimeric DNA polymerases of the invention described herein. The kits include any one of the compositions described herein and packaging material therefore. In other aspects the invention provides for nucleic acids and vectors encoding the chimeric DNA polymerases described herein and host cells transfected with vectors.

In a final aspect of the invention, the invention provides methods for DNA synthesis. The method includes, providing a chimeric DNA polymerase of any of the embodiments of the invention described herein, and contacting the chimeric DNA polymerase with a nucleic acid template wherein the chimeric DNA polymerase permits DNA synthesis.

I. Sso7d and Sso7d-Like Polypeptides

The chimeric DNA polymerases of the invention comprise a DNA biding domain having one or more mutations at amino acid positions 13, 16, 40, 41, 45, 55, 56, 61 or 63 of Sso7d (SEQ ID NO:2), or at a corresponding position in an Sso7d-like protein, e.g., Ssh7b (SEQ ID NO: 8), RiboP3 (SEQ ID NO: 9), Sto7e (SEQ ID NO: 12), Sac7d (SEQ ID NO: 12), Sac7e (SEQ ID NO: 14) and Sac7a (SEQ ID NO: 16).

Sso7d is a small, basic chromosomal protein from the hyperthermophilic archaeabacteria *Sulfolobus solfataricus*. It binds to DNA in a sequence-independent manner and when bound, increase the melting-temperature of DNA by up to 40° C. under some conditions (McAfee et al., Biochemistry 34:1006310077, 1995). The wild-type protein sequence is set forth in SEQ ID NO:2.

There are several known Sso7d-like proteins including, but not limited to, Sac7a, Sac7b, Sac7d, and Sac7e, from the hyperthermophilic archacabacteria *S. acidocaldarius*; and Ssh7a and Ssh7b, *Sulfolobus shibatae*. These proteins have an identity with Sso7d that ranges from 78% to 98%.

The mutated amino acid positions of a Sso7d protein or Sso7d-like protein are determined with reference to the Sso7d sequence as set forth in SEQ ID NO:2. Residues that can be mutated without negatively impacting the chimeric DNA polymerases of the invention have been identified through mutational studies described herein. In one embodiment, the amino acid residues are mutated at one or more of the following positions: glutamic acid to glutamine at position 13 of SEQ ID NO:2 (E13Q), isoleucine to threonine at position 16 of SEQ ID NO:2 (I16T), threonine to serine at position 40 of SEQ ID NO:2 (T40S), glycine to alanine at position 41 of SEQ ID NO:2 (G41A), valine to leucine at position 45 of SEQ ID NO:2 (V45L), leucine to valine at position of SEQ ID NO:2 (L55V), glutamine to aspartic acid at position 56 of SEQ ID NO:2 (Q56D), glutamine to glutamic acid at position 61 of SEQ ID NO:2 (Q61E) or lysine to arginine at position 63 of SEQ ID NO:2 (K63R), or a corresponding mutation in a Sso7d-like protein.

These designations indicate which amino acid residue in the claimed molecules are mutated. For example, E13Q indicates that the polypeptide of SEQ ID NO:2 is mutated at amino acid 13 of SEQ ID NO:2, resulting in a change from a glutamic acid to a glutamine. Similarly, a corresponding position or mutation in a Sso7d-like protein means that an equivalent amino acid in a Sso7d-like protein, e.g. Ssh7b, is mutated. The equivalent amino acid is identified when the Sso7d protein of SEQ ID NO:2 is maximally aligned with a Sso7d-like protein, e.g., Ssh7b. For example, E13 of Sso7d corresponds to E13 of Ssh7b (FIG. 1). Alignments can be performed either manually or using a sequence comparison algorithm, as described herein.

Changes to the amino acids at positions 13, 16, 40, 41, 45, 55, 56, 61 or 63 of SEQ ID NO:2 do not negatively effect the performance of the chimeric DNA polymerase of the invention. It was observed that many amino acids that vary between the Sso7d-like polypeptides could not be changed without negatively effecting the Sso7d-chimeric DNA polymerases. In addition, some of the amino acids which did not vary between the Sso7d like proteins could be changed without causing a loss of Sso7d-chimeric DNA polymerase functionality.

Amino acids at positions 13, 16, 40, 41, 45, 55, 56, 61 or 63 of SEQ ID NO:2 or at a corresponding amino acid in an Sso7d like protein can be substituted with a variety of amino acid residues. In one embodiment, the one or more mutations in the DNA binding domain include E13Q, I16T, T40S, G41A, V45L, L55V, Q56D, Q61E or K63R of SEQ ID NO:2.

In one embodiment, the chimeric DNA polymerase is mutated in the DNA binding domain at amino acid positions E13Q, I16T of SEQ ID NO:2 or at a corresponding amino acid in an Sso7d like protein.

In another embodiment, the chimeric DNA polymerase is mutated in the DNA binding domain at amino acid positions T40S, E13Q, I6T of SEQ ID NO:2 or at a corresponding amino acid in an Sso7d like protein.

In another embodiment, the chimeric DNA polymerase is mutated in the DNA binding domain at amino acid positions G41A, E13Q, I16T of SEQ ID NO:2 or at a corresponding amino acid in an Sso7d like protein.

In another embodiment, the chimeric DNA polymerase is mutated in the DNA binding domain at amino acid positions V45L, E13Q, I16T of SEQ ID NO:2 or at a corresponding amino acid in an Sso7d like protein.

In another embodiment, the chimeric DNA polymerase is mutated in the DNA binding domain at amino acid positions L55V, E13Q, I16T of SEQ ID NO:2 or at a corresponding amino acid in an Sso7d like protein.

In another embodiment, the chimeric DNA polymerase is mutated in the DNA binding domain at amino acid positions Q56D, E13Q, I16T of SEQ ID NO:2 or at a corresponding amino acid in an Sso7d like protein.

In another embodiment, the chimeric DNA polymerase is mutated in the DNA binding domain at amino acid positions Q56D, T40S, E13Q, I16T of SEQ ID NO:2 or at a corresponding amino acid in an Sso7d like protein.

In another embodiment, the chimeric DNA polymerase is mutated in the DNA binding domain at amino acid positions T40S, V45L, L55V, Q56D, K63R, E13Q, I16T of SEQ ID NO:2 or at a corresponding amino acid in an Sso7d like protein.

Typically the substituted amino acid residue is one that is conserved with the amino acid which is substituted. Often, the substituted residue occupies less volume than the amino acid residue in the native sequence. For example, the side chain of tryptophan occupies the largest volume of the naturally occurring amino acids. Tryptophan can therefore be substituted with less bulky amino acids, in particular such residues as alanine, glycine, or valine, that occupy less space. Further, a residue that introduces a major structural change into the polypeptide, e.g., proline, or has the capacity to introduce such a change, e.g., cysteine, is typically avoided. Charge and hydrophobicity may also be considered when substituting amino acids.

Other Sso7d-like portions can be identified based on their sequence homology to Sso7d. Typically, Sso7d-like proteins have about 78%, 80, 85, 90 or 95-98% amino acid sequence identity with Sso7d. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (e.g., overlapping positions)×100).

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention.

To obtain gapped alignments for comparison purposes and to identify amino acids in Sso7d that correspond to amino acids in Sso7d-like proteins, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad Sci. USA* 85:2444-2448. When using the FASTA algorithm for comparing nucleotide or amino acid sequences, a PAM120 weight residue table can, for example, be used with a k-tuple value of 2.

II. DNA Polymerases According to the Invention

The invention provides for chimeric DNA polymerase comprising a polymerase domain and a DNA binding domain. The polymerase domain can comprise a wild-type or a mutant DNA polymerase polypeptide. The DNA polymerases, useful according to the invention, can be with or without 3'-5' exonuclease activity, i.e., proofreading or non-proofreading, and are preferably thermostable.

Additional nucleic acid polymerases useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and φ29 DNA polymerase. The enzymes available commercially are: T4 (available from many sources e.g., Epicentre) and T7 (available from many sources, e.g. Epicentre for unmodified and USB for 3' to 5' exo⁻ T7 "Sequenase" DNA polymerase).

B. Archaeal DNA Polymerases:

There are 2 different classes of DNA polymerases which have been identified in archaea: 1. Family B/pol I type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol I or pol II) can be derived from archaea with optimal growth temperatures that are similar to the desired assay temperatures.

Thermostable archaeal DNA polymerases isolated from *Pyrococcus* species (*furiosus*, species GB-D, *woesii*, *abysii*, *horikoshii*), *Thermococcus* species (*kodakaraensis* KOD1, *litoralis*, species 9 degrees North-7, species JDF-3, *gorgonarius*), *Pyrodictium occultum*, and *Archaeoglobus fulgidus*. It is estimated that suitable archaea would exhibit maximal growth temperatures of >80-85° C. or optimal growth temperatures of >70-80° C. Appropriate PCR enzymes from the archaeal pol I DNA polymerase group are commercially available, including Pfu (Stratagene), KOD (Toyobo), Pfx (Life Technologies, Inc.), Vent (New England BioLabs), Deep Vent (New England BioLabs), Tgo (Roche), and Pwo (Roche).

Additional archaea DNA polymerases related to those listed above are described in the following references: Archaea: A Laboratory Manual (Robb, F. T. and Place, A. R., eds.), Cold Spring Harbor Laboratory Press, Cold Spring Harbor, N.Y., 1995 and *Thermophilic Bacteria* (Kristjansson, J. K., ed.) CRC Press, Inc., Boca Raton, Fla., 1992.

The invention therefore provides for thermostable archaeal DNA polymerases of either Family B/pol I type or pol II type as well as mutants or derivatives thereof.

In one embodiment of the invention, the DNA polymerase domain of the chimeric DNA polymerase comprises an archaeal DNA polymerase polypeptide. In a further embodiment, the archaeal DNA polymerase polypeptide is a Pfu DNA polymerase polypeptide. In yet another embodiment of the aspects described herein above, the chimeric DNA polymerase domain is at least 95% identical with the amino acid sequence of SEQ ID NO: 18.

TABLE 1

ACCESSION INFORMATION FOR CLONED FAMILY B POLYMERASES

Vent *Thermococcus litoralis*
ACCESSION AAA72101
PID      g348689
VERSION AAA72101.1 GI:348689
DBSOURCE locus THCVDPE accession M74198.1
THEST *THERMOCOCCUS* SP. (STRAIN TY)

TABLE 1-continued

ACCESSION INFORMATION FOR CLONED FAMILY B POLYMERASES

ACCESSION O33845
PID    g3913524
VERSION O33845 GI:3913524
DBSOURCE swissprot: locus DPOL_THEST, accession O33845
Pab *Pyrococcus abyssi*
ACCESSION P77916
PID    g3913529
VERSION P77916 GI:3913529
DBSOURCE swissprot: locus DPOL_PYRAB, accession P77916
PYRHO *Pyrococcus horikoshii*
ACCESSION O59610
PID    g3913526
VERSION O59610 GI:3913526
DBSOURCE swissprot: locus DPOL_PYRHO, accession O59610
PYRSE *PYROCOCCUS* SP. (STRAIN GE23)
ACCESSION P77932
PID    g3913530
VERSION P77932 GI:3913530
DBSOURCE swissprot: locus DPOL_PYRSE, accession P77932
DeepVent *Pyrococcus* sp.
ACCESSION AAA67131
PID    g436495
VERSION AAA67131.l GI:436495
DBSOURCE locus PSU00707 accession U00707.1
Pfu *Pyrococcus furiosus*
ACCESSION P80061
PID    g399403
VERSION P80061 GI:399403
DBSOURCE swissprot: locus DPOL_PYRFU, accession P80061
JDF-3 *Thermococcus* sp.
Unpublished
Baross gi|2097756|pat|US|560201|12 Sequence 12
from patent US 5602011
9degN *THERMOCOCCUS* SP. (STRAIN 9ON-7).
ACCESSION Q56366
PID    g3913540
VERSION Q56366 GI:3913540
DBSOURCE swissprot: locus DPOL_THES9, accession Q56366
KOD *Pyrococcus* sp.
ACCESSION BAA06142
PID    g1620911
VERSION BAA06142.l GI:1620911
DBSOURCE locus PYWKODPOL accession D29671.1
Tgo *Thermococcus gorgonarius.*
ACCESSION 4699806
PID    g4699806
VERSION GI:4699806
DBSOURCE pdb: chain 65, release Feb. 23, 1999
THEFM *Thermococcus fumicolans*
ACCESSION P74918
PID    g3913528
VERSION P74918 GI:3913528
DBSOURCE swissprot: locus DPOL_THEFM, accession P74918
METTH *Methanobacterium thermoautotrophicum*
ACCESSION O27276
PID    g3913522
VERSION O27276 GI:3913522
DBSOURCE swissprot: locus DPOL_METTH, accession O27276
Metja *Methanococcus jannaschii*
ACCESSION Q58295
PID    g3915679
VERSION Q58295 GI:3915679
DBSOURCE swissprot: locus DPOL_METJA, accession Q58295
POC *Pyrodictium occultum*
ACCESSION B56277
PID    g1363344
VERSION B56277 GI:1363344
DBSOURCE pir: locus B56277
ApeI *Aeropyrum pernix*
ACCESSION BAA81109
PID    g5105797
VERSION BAA81lO9.1 GI:5105797
DBSOURCE locus AP000063 accession AP000063.1
ARCFU *Archaeoglobus fulgidus*
ACCESSION O29753
PID    g3122019

TABLE 1-continued

ACCESSION INFORMATION FOR CLONED FAMILY B POLYMERASES

VERSION O29753 GI:3122019
DBSOURCE swissprot: locus DPOL_ARCFU, accession O29753
*Desulfurococcus* sp. Tok.
ACCESSION 6435708
PID    g64357089
VERSION GT:6435708
DBSOURCE pdb. chain 65, release Jun. 2, 1999

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol II catalytic subunit lacks 5' to 3' exonuclease activity, but in some cases 3' to 5' exonuclease activity is located in the same polypeptide.

There are a variety of commercially available Pol I DNA polymerases, some of which have been modified to reduce or abolish 5' to 3' exonuclease activity.

Suitable thermostable pol I DNA polymerases can be isolated from a variety of thermophilic eubacteria, including *Thermus species* and *Thermotoga maritima* such as *Thermus aquaticus* (Taq), *Thermus thermophilus* (Tth) and *Thermotoga maritima* (Tma UlTma).

Additional eubacteria related to those listed above are described in *Thermophilic Bacteria* (Kristjansson, J. K., ed.) CRC Press, Inc., Boca Raton, Fla., 1992.

In one embodiment, the chimeric DNA polymerase comprises a polymerase domain comprising a Taq DNA polymerase polypeptide.

The invention further provides for DNA polymerases that are chemically modified according to methods disclosed in U.S. Pat. Nos. 5,677,152, 6,479,264 and 6,183, 998, the contents of which are hereby incorporated by reference in their entirety.

D. Mutant DNA Polymerases for Use in the Chimeric DNA Polymerases of the Invention.

According to the invention, chimeric DNA polymerases can be generated from any DNA polymerase either wild-type or modified to contain one or more mutations, including but not limited to, one or more point mutations, N- and/or C-truncations, internal deletion or insertion that would cause the DNA polymerase to behave differently than the wild-type polymerase. DNA polymerase mutations useful to the invention include, but are not limited to, mutations that confer base analog or uracil insensitivity, improve nucleotide analog incorporation, increase fidelity, eliminate 3'-5' exonuclease activity or eliminate 5'-3' exonuclease activity or reduce polymerase activity. Specific examples of useful mutations or truncations include but are not limited to, V93R,K,E,D in Pfu DNA polymerase, which confer uracil insensitivity, D141A/E143A in Pfu DNA polymerase, which eliminates 3'-5' exonuclease activity, and the N-terminal truncation of Taq DNA polymerase to eliminate 5'-3' exonuclease activity (KlenTaq). Methods for generating DNA polymerase mutants are described below and other methods are known in the art.

The amino acid and DNA coding sequence of a wild-type Pfu DNA polymerase are shown in SEQ ID NO:18 (Genbank Accession # P80061). A detailed description of the structure and function of Pfu DNA polymerase can be found, among other places in U.S. Pat. Nos. 5,948,663; 5,866,395; 5,545,552; 5,556,772, all of which are hereby incorporated in their entirety by reference. A non-limiting detailed procedure for preparing Pfu DNA polymerase with, for example, reduced uracil detection activity is provided in U.S. Patent Publication No. 2004/0197800 (filed Nov. 5, 2003) which is herein incorporated by reference in its entirety The invention provides for chimeric DNA polymerases comprising a DNA polymerase domain with one or more mutations that reduce base analog detection activity as disclosed in the pending U.S. Patent Publication No.: 2004/0091873 (Hogrefe et al.; filed Nov. 18, 2002), the contents of which are hereby incorporated in their entirety.

In one embodiment, the chimeric DNA polymerases comprises a Pfu DNA polymerase polypeptide domain containing a Valine to Arginine, Valine to Glutamic acid, Valine to Lysine, Valine to Aspartic Acid or Valine to Asparagine substitution at amino acid position 93.

The invention further provides for chimeric DNA polymerases comprising a V93 mutant Pfu DNA polymerases polypeptide with reduced uracil detection activity that contain one or more mutations that reduce DNA polymerization as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. Patent Publication No.: 2003/0180741 (Hogrefe et al.; filed Jul. 30, 2002); and the pending U.S. Patent Publication No.: 2003/0143577 (Hogrefe et al.; filed Aug. 23, 2002), the contents of which are hereby incorporated in their entirety.

In one embodiment, the invention provides for chimeric DNA polymerases comprising a Pfu DNA polymerase domain with a G387P mutation. In a further embodiment, the invention provides for chimeric DNA polymerases comprising a Pfu DNA polymerase domain with V93R/G387P, V93E/G387P, V93D/G387P, V93K/G387P or V93N/G387P double mutants with reduced DNA polymerization activity and reduced uracil detection activity.

The invention further provides for chimeric DNA polymerases comprising a Pfu DNA polymerase domain with V93R, V93E, V93D, V93K or V93N mutations resulting in reduced uracil detection activity and further containing one or mutations that reduce or eliminate 3'-5' exonuclease activity as disclosed in the pending U.S. patent application Ser. No. 09/698,341 (Sorge et al; filed Oct. 27, 2000).

In one embodiment, the invention provides for a chimeric DNA polymerase comprising a polymerase domain having a V93R/D141A/E143A triple mutant Pfu DNA polymerase with reduced 3'-5' exonuclease activity and reduced uracil detection activity.

Methods used to generate Pfu DNA polymerases with reduced DNA polymerization activity of the invention are disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety.

Methods used to generate 3'-5' exonuclease deficient JDF-3 DNA polymerases including the D141A and E143A mutations are disclosed in the pending U.S. patent application Ser. No. 09/698,341 (Sorge et al; filed Oct. 27, 2000). A person skilled in the art in possession of the teachings of the pending U.S. patent application Ser. No. 09/698,341 (Sorge et al; filed Oct. 27, 2000) would have no difficulty introducing both the corresponding D141A and E143A mutations or other 3'-5' exonuclease mutations into a DNA polymerase of the invention including for example, the non-chimeric V93 Pfu DNA polymerase cDNA, as disclosed in the pending U.S. patent application Ser. No. 09/698,341, using established site-directed mutagenesis methodology.

III. Preparing DNA Polymerase Polypeptide Mutants and DNA Binding Polypeptide Mutants for Use in the Chimeric DNA Polymerases of the Invention.

The DNA binding domains and polymerase domains of the chimeric DNA polymerases of the invention may contain numerous amino acid changes or mutations. One of skill in the art will recognize that there are numerous ways of generating mutations which result in the appropriate amino acid change. Such well-known methods include site-directed mutagenesis, PCR amplification using degenerate oligonucleotides, chemical synthesis of a desired oligonucleotide (e.g., in conjunction with ligation and/or cloning to generate large nucleic acids) and other well-known techniques. See, Giliman & Smith, Gene 8:81-97 (1979), Roberts, et al., Nature 328:731-734 (1987) and Sambrook, Innis, and Ausubel (all supra).

For example, a mutated Sso7d binding domain polypeptide can be generated by genetic modification (e.g., by modifying the DNA sequence of a wild-type Sso7d polypeptide). A number of methods are known in the art that permit the random as well as targeted mutation of DNA sequences (see for example, Ausubel et. al. *Short Protocols in Molecular Biology* (1995) $3^{rd}$ Ed. John Wiley & Sons, Inc.). In addition, there are a number of commercially available kits for site-directed mutagenesis, including both conventional and PCR-based methods. Examples include the QUIKCHANGE® Site-directed mutagenesis Kit from Stratagene (Catalog No. 200518).

In addition DNA binding domains may be generated by insertional mutation or truncation (N-terminal, internal or C-terminal) according to methodology known to a person skilled in the art.

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease Dpn I (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase. Further examples of mutagenesis protocols are described, herein in Example 1.

A non-limiting example for the isolation of a mutated DNA binding proteins or polymerase is described in detail as follows:

Plasmid template DNA (approximately 0.5 pmole) is added to a PCR cocktail containing: 1× mutagenesis buffer (20 mM Tris HCl, pH 7.5; 8 mM $MgCl_2$; 40 µg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 µM each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5 U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* according to standard methods.

Once the mutated DNA binding or polymerase polypeptides are generated they are evaluated using techniques known in the art and those described herein.

Genes for desired mutant DNA binding polypeptides and mutant polymerase polypeptides generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

In one embodiment, the invention provides for chimeric DNA polymerase comprising a DNA binding domain and a polymerase domain, wherein said DNA binding domain has one or more mutations at an amino acid corresponding to position 13, 16, 40, 41, 45, 55, 56, 61 or 63 of SEQ ID NO:2.

In another embodiment, the invention provides for chimeric DNA polymerases, wherein one or more mutations are selected from the group consisting of E13Q, I16T, T40S, G41A, V45L, L55V, Q56D, Q61E and K63R.

IV. Production of Chimeric DNA Polymerases

The chimeric DNA polymerases of the invention are DNA polymerase fusion polypeptides having at least two polypeptides covalently linked, in which one polypeptide comes from one protein sequence or domain, e.g., DNA polymerase, and the other polypeptide comes from another protein sequence or domain, e.g., DNA binding protein. The DNA binding domain and the polymerase domain, of the chimeric DNA polymerase of the invention, can be joined by methods well known to those of skill in the art. These methods include both chemical and recombinant means.

Nucleic acids encoding the domains to be incorporated into the chimeric DNA polymerases of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

Nucleic acid sequences that encode the DNA binding polypeptides and polymerase polypeptides can be obtained using any of a variety of methods. In some embodiments, the nucleic acid sequences encoding the polypeptides are cloned from cDNA and genomic DNA libraries by hybridization with probes, or isolated using amplification techniques with oligonucleotide primers. More commonly, amplification techniques are used to amplify and isolate the DNA binding domain and polymerase sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding catalytic or double-stranded nucleic acid binding domains can also be isolated from expression libraries using antibodies as probes. Other suitable methods for isolating the DNA binding domain and polymerase domain of the present invention are described herein.

The polypeptides can be linked either directly or via a covalent linker, e.g., an amino acid linker, such as a polyglycine linker, or another type of chemical linker, e.g., a carbohydrate linker, a lipid linker, a fatty acid linker, a polyether linker, e.g., PEG, etc. (See, e.g., Hermanson, Bioconjugate techniques (1996)). The polypeptides forming the fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a DNA polymerase of the invention. The polypeptides of the fusion protein can be in any order. The chimeric DNA polymerases, may be produced by covalently linking a chain of amino acids from one protein sequence, e.g., Pfu, to a chain of amino acids from another protein sequence, e.g., mutant Sso7d, by preparing a recombinant polynucleotide contiguously encoding the fusion protein.

The different chains of amino acids in a fusion protein may be directly spliced together or may be indirectly spliced together via a chemical linking group or an amino acid linking group, which can be about 200 amino acids or more in length, with 1 to 100 amino acids being typical. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

Methods of preparing a chimeric DNA polymerases of the invention are also described in WO 01/92501 A1, United States Publication No. 2004/0081963 (filed Oct. 23, 2002) and Pavlov et al., 2002, Proc. Natl. Acad. Sci. USA, 99:13510-13515, which are herein incorporated in their entirety.

In one embodiment, the chimeric DNA polymerase of the invention comprises a wild-type DNA polymerase linked to a mutated DNA binding protein.

In another embodiment, the chimeric DNA polymerase of the invention comprises a mutated DNA polymerase linked to a mutated DNA binding protein.

V. Expressing Chimeric DNA Polymerases of the Invention

Methods known in the art may be applied to express and isolate the chimeric DNA polymerases of the invention. Many bacterial expression vectors contain sequence elements or combinations of sequence elements allowing high level inducible expression of the protein encoded by a foreign sequence. For example, bacteria expressing an integrated inducible form of the T7 RNA polymerase gene may be transformed with an expression vector bearing a chimeric DNA polymerase construct linked to the T7 promoter. Induction of the T7 RNA polymerase by addition of an appropriate inducer, for example, isopropyl-β-D-thiogalactopyranoside (IPTG) for a lac-inducible promoter, induces the high level expression of the chimeric DNA polymerase from the T7 promoter.

Appropriate host strains of bacteria may be selected from those available in the art by one of skill in the art. As a non-limiting example, E. coli strain BL-21 is commonly used for expression of exogenous proteins since it is protease deficient relative to other strains of E. coli. BL-21 strains bearing an inducible T7 RNA polymerase gene include WJ56 and ER2566 (Gardner & Jack, 1999, supra). For situations in which codon usage for the particular polymerase gene differs from that normally seen in E. coli genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUS™ cell strains carrying rare-codon tRNAs are available from Stratagene, for example).

There are many methods known to those of skill in the art that are suitable for the purification of a chimeric DNA polymerase of the invention. For example, the method of Lawyer et al. (1993, PCR Meth. & App. 2: 275) is well suited for the isolation of chimeric DNA polymerases expressed in E. coli, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase. Further, the chimeric DNA polymerases may be isolated by an ammonium sulfate fractionation, followed by Q Sepharose and DNA cellulose columns, or by adsorption of contaminants on a HiTrap Q column, followed by gradient elution from a HiTrap heparin column.

VI. Applications of the Invention

In one aspect, the invention provides a method for DNA synthesis using the compositions of the subject invention. Typically, synthesis of a polynucleotide requires a synthesis primer, a synthesis template, polynucleotide precursors for incorporation into the newly synthesized polynucleotide, (e.g. dATP, dCTP, dGTP, dTTP), and the like. Detailed methods for carrying out polynucleotide synthesis are well known to the person of ordinary skill in the art and can be found, for example, in *Molecular Cloning second edition*, Sambrook et al., Cold Spring Harbor Laboratory Press, Cold Spring Harbor, N.Y. (1989).

"Polymerase chain reaction" or "TCR" refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. Patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

For ease of understanding the advantages provided by the present invention, a summary of PCR is provided. The PCR reaction involves a repetitive series of temperature cycles and is typically performed in a volume of 50-100 µl. The reaction mix comprises dNTPs (each of the four deoxynucleotides DATP, dCTP, dGTP, and dTTP), primers, buffers, DNA polymerase, and polynucleotide template. PCR requires two primers that hybridize with the double-stranded target polynucleotide sequence to be amplified. In PCR, this double-stranded target sequence is denatured and one primer is annealed to each strand of the denatured target. The primers anneal to the target polynucleotide at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237-238 and Kwok, and Orrego, in: Innis et al. eds., 1990, *PCR Pro-* tocols: A Guide to Methods and Applications, Academic Press, Inc., San Diego, Calif., which are incorporated herein by reference.

A. Thermostable Enzymes

For PCR amplifications, the chimeric DNA polymerase of the invention may comprise a polymerase domain comprising a thermostable polymerase. As used herein, "thermostable" refers to an enzyme which is stable to heat, is heat resistant, and functions at high temperatures, e.g., 50 to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from 85° C., for shorter polynucleotides, to 105° C. for a time depending mainly on the temperature and the polynucleotide length, typically from 0.25 minutes for shorter polynucleotides, to 4.0 minutes for longer pieces of DNA. Higher temperatures may be tolerated as the buffer salt concentration and/or GC composition of the polynucleotide is increased. Preferably, the enzyme will not become irreversibly denatured at 90 to 100° C. An enzyme that does not become irreversibly denatured, according to the invention, retains at least 10%, or at least 25%, or at least 50% or more function or activity during the amplification reaction.

B. PCR Reaction Mixture

In addition to the chimeric DNA polymerase of the invention, one of average skill in the art may also employ other PCR parameters to increase the fidelity of synthesis/amplification reaction. It has been reported PCR fidelity may be affected by factors such as changes in dNTP concentration, units of enzyme used per reaction, pH, and the ratio of $Mg^{2+}$ to dNTPs present in the reaction (Mattila et al., 1991, supra).

$Mg^{2+}$ concentration affects the annealing of the oligonucleotide primers to the template DNA by stabilizing the primer-template interaction, it also stabilizes the replication complex of polymerase with template-primer. It can therefore also increase non-specific annealing and produce undesirable PCR products (gives multiple bands in gel). When non-specific amplification occurs, $Mg^{2+}$ may need to be lowered or EDTA can be added to chelate $Mg^{2+}$ to increase the accuracy and specificity of the amplification.

Other divalent cations such as $Mn^{2+}$, or $Co^{2+}$ can also affect DNA polymerization. Suitable cations for each DNA polymerase are known in the art (e.g., in *DNA Replication $2^{nd}$ edition*, supra). Divalent cation is supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, preferably, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Monovalent cation required by DNA polymerase may be supplied by the potassium, sodium, ammonium, or lithium salts of either chloride or acetate. For KCl, the concentration is between 1 and 200 mM, preferably the concentration is between 40 and 100 mM, although the optimum concentration may vary depending on the polymerase used in the reaction.

Deoxyribonucleotide triphosphates (dNTPs) are added as solutions of the salts of dATP, dCTP, dGTP, dUTP, and dTTP, such as disodium or lithium salts. In the present methods, a final concentration in the range of 1 µM to 2 mM each is suitable, and 100-600 µM is preferable, although the optimal concentration of the nucleotides may vary in the PCR reaction depending on the total dNTP and divalent metal ion concentration, and on the buffer, salts, particular primers, and template. For longer products, i.e., greater than 1500 bp, 500 µM each dNTP may be preferred when using a Tris-HCl buffer.

dNTPs chelate divalent cations, therefore amount of divalent cations used may need to be changed according to the dNTP concentration in the reaction. Excessive amount of dNTPs (e.g., larger than 1.5 mM) can increase the error rate and possibly inhibit DNA polymerases. Lowering the dNTP (e.g., to 10-50 µM) may therefore reduce error rate. PCR reaction for amplifying larger size template may need more dNTPs.

One suitable buffering agent is Tris-base/Tris-HCl or Tris-base/Tris-$H_2SO_4$, preferably pH 10, although the pH may be in the range 8.0-11.5. The Tris-base/Tris-HCl or Tris-base/Tris-$H_2SO_4$ concentration is from 5-250 mM, although 10-100 mM is most preferred.

PCR is a very powerful tool for DNA amplification and therefore very little template DNA is needed. However, in some embodiments, to reduce the likelihood of error, a higher DNA concentration may be used, though too many templates may increase the amount of contaminants and reduce efficiency.

Usually, up to 3 µM of primers may be used, but high primer to template ratio can results in non-specific amplification and primer-dimer formation. Therefore it is usually necessary to check primer sequences to avoid primer-dimer formation.

The invention provides for chimeric DNA polymerases comprising a polymerase domain with a Pfu V93R, V93E, V93K, V93D, or V93N DNA polymerases with reduced uracil detection activity that enhance PCR of GC rich DNA templates by minimizing the effect of cytosine deamination in the template and by allowing the use of higher denaturation times and denaturation temperatures.

C. Cycling Parameters

Denaturation time may be increased if template GC content is high. Higher annealing temperature may be needed for primers with high GC content or longer primers. Gradient PCR is a useful way of determining the annealing temperature. Extension time should be extended for larger PCR product amplifications. However, extension time may need to be reduced whenever possible to limit damage to enzyme.

The number of cycle can be increased if the number of template DNA is very low, and decreased if high amount of template DNA is used.

D. PCR Enhancing Factors

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR additives may also affect the accuracy and specificity of PCR reactions. EDTA less than 0.5 mM may be present in the amplification reaction mix. Detergents such as Tween-20™ and Nonide™ P-40 are present in the enzyme dilution buffers. A final concentration of non-ionic detergent approximately 0.1% or less is appropriate, however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. BSA (up to 0.8 µg/µl) can improve efficiency of PCR reaction. Betaine (0.5-2M) is also useful for PCR over high GC content and long fragments of DNA. Tetramethylammonium chloride (TMAC, >50 mM), Tetraethylammonium chloride (TEAC), and Trimethlamine N-oxide (TMANO) may also be used. Test PCR reactions may be performed to determine optimum concentration of each additive mentioned above.

The invention provides for additives including, but not limited to antibodies (for hot start PCR) and ssb (single strand DNA binding protein; higher specificity). The invention also contemplates mutant archael DNA polymerases in combination with accessory factors, for example as described in U.S. Pat. No. 6,333,158, and WO 01/09347 A2, hereby incorporated by reference in its entirety.

Various specific PCR amplification applications are available in the art (for reviews, see for example, Erlich, 1999, *Rev Immunogenet.*, 1: 127-34; Prediger 2001, *Methods Mol. Biol.* 160:49-63; Jurecic et al., 2000, *Curr. Opin. Microbiol.* 3:316-21; Triglia, 2000, *Methods Mol. Biol.* 130:79-83; MaClelland et al., 1994, *PCR Methods Appl.* 4:S66-81; Abramson and Myers, 1993, *Current Opinion in Biotechnology* 4:41-47; each of which is incorporated herein by references).

The subject invention can be used in PCR applications including, but not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be used to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be used as a control to verify the quality of PCR; x) Q/C-PCR (Quantitative comparative) which uses an internal control DNA sequence (but of a different size) which competes with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis.

Additional methods of using the chimeric DNA polymerases of the present invention are described in U.S. Publication No. 2005/0048530 filed Mar. 19, 2004 are herein incorporated by reference in its entirety.

It should be understood that this invention is not limited to any particular amplification system. As other systems are developed, those systems may benefit by practice of this invention.

VII. Kits

The invention herein also contemplates a kit format which comprises a package unit having one or more containers of the subject composition and in some embodiments including containers of various reagents used for polynucleotide synthesis, including synthesis in PCR. The kit may also contain one or more of the following items: polynucleotide precursors, primers, buffers, instructions, and controls. Kits may include containers of reagents mixed together in suitable proportions for performing the methods in accordance with the invention. Reagent containers preferably contain reagents in unit quantities that obviate measuring steps when performing the subject methods.

The invention contemplates a kit comprising a combination of chimeric DNA polymerases according to the invention, PCR enhancing reagents and reagents for PCR amplification, DNA sequencing or mutagenesis.

A kit for sequencing DNA will comprise a number of container means. A first container means may, for example, comprise a substantially purified sample of the polymerases of the invention. A second container means may comprise one or a number of types of nucleotides needed to synthesize a DNA molecule complementary to DNA template. A third container means may comprise one or a number of different types of terminators (such as dideoxynucleoside triphosphates). A fourth container means may comprise pyrophosphatase. In addition to the above container means, additional container means may be included in the kit which comprise one or a number of primers and/or a suitable sequencing buffer.

A kit used for amplifying or synthesis of nucleic acids will comprise, for example, a first container means comprising a substantially pure chimeric DNA polymerase of the invention and one or a number of additional container means which comprise a single type of nucleotide or mixtures of nucleotides.

A kit used for mutagenesis of nucleic acids may comprise, for example, a first container means comprising a substantially pure chimeric DNA polymerase of the invention. A second container means may comprise a single type of nucleotide or mixture of nucleotides. A third container means may comprises a suitable reaction buffer. An additional container means may comprise competent cells.

Various primers may be included in a kit as well as a suitable amplification or synthesis buffers.

When desired, the kit of the present invention may also include container means which comprise detectably labeled nucleotides which may be used during the synthesis or sequencing of a nucleic acid molecule. One of a number of labels may be used to detect such nucleotides. Illustrative labels include, but are not limited to, radioactive isotopes, fluorescent labels, chemiluminescent labels, bioluminescent labels and enzyme labels.

Having now generally described the invention, the same will be more readily understood through reference to the following Examples which are provided by way of illustration, and are not intended to be limiting of the present invention, unless specified.

EXAMPLES

Example 1

Construction of DNA Chimeric Polymerases Having a Pfu DNA Polymerase Domain and a Sso7d DNA Binding Domain A Pfu-Sso7d fusion was created by joining the N-terminus of Sso7d to the C-terminus of *Pyrococcus furiosus* DNA polymerase (Pfu). A linker sequences of six amino acids (Gly-Thr-Gly-Gly-Gly-Gly) was added to the N-terminus of Sso7d. The nucleic acid and amino acid sequences encoding the wild-type Pfu-Sso7d chimera are shown in SEQ ID Nos: 18 and 20 respectively.

Point mutations were introduced into the Sso7d portion of the Pfu DNA polymerase chimera via the QuickChange Site-Directed Mutagenesis Kit (Stratagene Catalog #200518) according to manufacturer's instructions.

Briefly, each mutation was introduced by a PCR reaction using a set of primers complementary (except for the point mutation) to opposite strands of the Sso7d sequence in the region of the desired mutation. Cycling conditions were 95° C. for 2 minutes for 1 cycle; 95° C. for 30 seconds, 58° C. for 30 seconds, 68° C. for 10 minutes for 18 cycles; and 68° C. for 10 minutes for 1 cycle. The reaction was then treated with DPN I to degrade the non-mutated plasmid. XL-10 Gold super competent cells were transformed with the mutated plasmid and plated. Plasmid preparations of the mutant plasmid were sequenced to confirm the addition of the mutations. The following sets of mutations were introduced into the Sso7d portion of the Pfu DNA polymerase chimera:
1. K4R, E13Q, I16T of SEQ ID NO:2
2. T2S, E13Q, I16T of SEQ ID NO:2
3. A1V, E13Q, I16T of SEQ ID NO:2
4. E13Q, I16T of SEQ ID NO:2
5. W23, E13Q, I16T of SEQ ID NO:2
6. I29V, E13Q, I16T of SEQ ID NO:2
7. T32S, E13Q, I16T of SEQ ID NO:2
8. E35D, E13Q, I16T of SEQ ID NO:2
9. G37A, E13Q, I16T of SEQ ID NO:2
10. T40S, E13Q, I16T of SEQ ID NO:2
11. G41A, E13Q, I16T of SEQ ID NO:2
12. V45L, E13Q, I16T of SEQ ID NO:2
13. L55V, E13Q, I16T of SEQ ID NO:2
14. Q56D, E13Q, I16T of SEQ ID NO:2
15. Q56D, T40S, E13Q, I16T of SEQ ID NO:2
16. T40S, V45L, L55V, Q56D, K63R, E13Q, I16T of SEQ ID NO:2

Example 2

Comparison of DNA Processivity of DNA Polymerase Chimeras

In order to determine the effect of the mutations on the amplified product yield a PCR amplification reaction was performed comparing each mutant Sso7d-Pfu DNA polymerase chimera with the wild-type Sso7d-Pfu DNA polymerase chimera.

The PCR reactions contained from 12.5 ng to 100 ng of the mutant or wild-type chimeric DNA polymerase, pH10 PCR reaction buffer, 200 µM of each dNTP, 100 ng of each forward and reverse primer specific for human alpha-1 anti-trypsin and 100 ng of genomic DNA. The reaction was performed in a thermal cycler under the following cycling parameters: 95° C. for 2 minutes for 1 cycle; 95° C. for 10 seconds, 58° C. for 5 seconds, and 72° C. for 10 seconds for 30 cycles. The amplified products were analyzed on an agarose gel to assess their relative yields.

DNA gel shift assay were performed to compare the DNA binding ability of each of the mutated Sso7d-Pfu DNA polymerase chimeras to the wild-type Sso7d-Pfu DNA polymerase chimera. Each Sso7d-Pfu DNA polymerase chimera (from 100 to 600 ng) was incubated in separate reaction mixtures at room temperature for 10 minutes. The reaction mixtures also contained 100 ng of genomic DNA in Pfu DNA polymerase reaction buffer. The reaction mixtures were run and analyzed on a 6% agarose gel to assess the DNA binding ability of the chimeric Sso7d-Pfu DNA polymerase.

The results indicated that only a limited number of amino acids could be changed without causing a loss of Sso7d functionality in the DNA polymerase chimera. Furthermore, certain regions of the Sso7d protein were more accommodating to amino acid changes than others.

Amino acid changes (A1V, T2K, T2S, and K4R) introduced at the N-terminus of the Sso7d portion of the DNA polymerase chimera resulted in reduced PCR yield and DNA binding activity when compared to the wild-type construct in PCR amplification and genomic DNA gel shift assays. No decrease in PCR yield or DNA binding activity was observed with amino acid changes E13Q and I16T.

Amino acid changes (W23F, I29, T32S, E35D, and G37A) introduced in the Sso7d portion of the DNA polymerase chimera decreased PCR yield and DNA binding activity of the chimera when compared to the wild-type construct. W23F and T32S are conserved amino acids while I29, E35, and G37 are non-conserved amino acids. The non-conserved amino acid I29 was changed to I29V, I29L and I29A. Amino acids L and A are structurally very similar to I and yet all changes resulted in a functionally deficient chimera when compared to the wild-type construct.

No decrease in PCR yield and DNA binding activity was observed when amino acid changes T40S, G41A and V45L were made to the Sso7d portion of the DNA polymerase chimera. Mutation of the non-conserved amino acid L55 to V also had no negative effect on chimera functionality even though the amino acid change L55V was different than the amino acid at this site in Sac7e. Mutations made in the C-terminal alpha helix of the Sso7d portion of the chimeric DNA polymerase (Q56D, Q61E, and K63R) did not cause a loss of functionality to the chimera.

A chimeric DNA polymerase with an Sso7d domain having mutations at E13Q, I16T, T40S, V45L, L55V, Q56D, and K63R had comparable DNA yield and DNA binding activity to the wild-type chimeric DNA polymerase. (FIG. 3)

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A chimeric DNA polymerase comprising a DNA binding domain and a polymerase domain, wherein said DNA binding domain has the wild-type sequence of Sso7d (SEQ ID NO:2) or of a wild-type Sso7d-like protein selected from the group consisting of Ssh7b (SEQ ID NO:8), RiboP3 (SEQ ID NO:9), Stole (SEQ ID NO:10), Sac7d (SEQ ID NO:12), Sac7e (SEQ ID NO:14), and Sac7a (SEQ ID NO:16), with the exception of seven, eight, or nine substitution mutations at positions corresponding to seven, eight, or all nine of the following amino acid positions: 13, 16, 40, 41, 45, 55, 56, 61, and 63 of SEQ ID NO:2.

2. The chimeric DNA polymerase of claim 1, wherein said substitution mutations are selected from the group consisting of:
   an E or Q the position corresponding to position 13 of SEQ ID NO:2;
   an I or T at the position corresponding to position 16 of SEQ ID NO:2;
   a T or S at the position corresponding to position 40 of SEQ ID NO:2;
   a G or A at the position corresponding to position 41 of SEQ ID NO:2;
   a V or L at the position corresponding to position 45 of SEQ ID NO:2;
   an L or V at the position corresponding to position 55 of SEQ ID NO:2;
   a Q or D at the position corresponding to position 56 of SEQ ID NO:2;
   a Q or E at the position corresponding to position 61 of SEQ ID NO:2; and
   a K or R at the position corresponding to position 63 of SEQ ID NO:2.

3. A chimeric DNA polymerase comprising a DNA binding domain and a polymerase domain, wherein said DNA binding domain has the sequence of Sso7d (SEQ ID NO:2) or of a wild-type Sso7d-like protein selected from the group consisting of Ssh7b (SEQ ID NO:8), RiboP3 (SEQ ID NO:9), Stole (SEQ ID NO:10), Sac7d (SEQ ID NO:12), Sac7e (SEQ ID NO:14), and Sac7a (SEQ ID NO:16), with the exception of seven substitution mutations at the positions corresponding to amino acid positions 13, 16, 40, 45, 55, 56, and 63 of SEQ ID NO:2.

4. The chimeric DNA polymerase of claim 3, wherein said substitution mutations are selected from the group consisting of:
   an E or Q the position corresponding to position 13 of SEQ ID NO:2;
   an I or T at the position corresponding to position 16 of SEQ ID NO:2;
   a T or S at the position corresponding to position 40 of SEQ ID NO:2;
   a V or L at the position corresponding to position 45 of SEQ ID NO:2;
   an L or V at the position corresponding to position 55 of SEQ ID NO:2;
   a Q or D at the position corresponding to position 56 of SEQ ID NO:2;
   a K or R at the position corresponding to position 63 of SEQ ID NO:2.

5. A chimeric DNA polymerase comprising a DNA binding domain and a polymerase domain, wherein said DNA binding domain comprises the amino acid sequence of SEQ ID NO:4.

6. A chimeric DNA polymerase comprising a DNA binding domain and a polymerase domain, wherein said DNA binding domain has the sequence of Sso7d (SEQ ID NO:2) or of a wild-type Sso7d-like protein selected from the group consisting of Ssh7b (SEQ ID NO:8), RiboP3 (SEQ ID NO:9), Stole (SEQ ID NO:10), Sac7d (SEQ ID NO:12), Sac7e (SEQ ID NO:14), and Sac7a (SEQ ID NO:16), with the exception of nine substitution mutations at the positions corresponding to amino acid positions 13, 16, 40, 41, 45, 55, 56, 61 and 63 of SEQ ID NO:2.

7. The chimeric DNA polymerase of claim 1, wherein said polymerase domain comprises an archaeal DNA polymerase.

8. The chimeric DNA polymerase of claim 1, wherein said polymerase domain has thermally stable polymerase activity.

9. The chimeric DNA polymerase of claim 1, wherein said polymerase domain comprises a Pfu DNA polymerase.

10. The chimeric DNA polymerase of claim 9, wherein said polymerase domain is at least 95% identical with the amino acid sequence of SEQ ID NO:18.

11. The chimeric DNA polymerase of claim 1, wherein said polymerase domain comprises a Taq DNA polymerase.

12. A chimeric DNA polymerase comprising the amino acid sequence of SEQ ID NO:20.

13. A composition comprising the DNA polymerase of claim 1, or 12.

14. A kit comprising the chimeric DNA polymerase of claim 1, or 12, and packaging materials therefor.

15. A method for DNA synthesis comprising:
   a) providing a chimeric DNA polymerase according to claim 1, or 12; and
   b) contacting said chimeric DNA polymerase with a nucleic acid template, wherein said enzyme permits DNA synthesis.

16. The chimeric DNA polymerase of claim 1, wherein said polymerase domain comprises a mutant polymerase.

17. The chimeric DNA polymerase of claim 16, wherein said mutant polymerase has V93R, V93E, V93D, V93K or V93N mutations resulting in reduced uracil detection activity.

18. The chimeric DNA polymerase of claim 16, wherein said mutant polymerase has D141A and/or E143A mutations resulting in reduced 3'-5' exonuclease activity.

19. The chimeric DNA polymerase of claim 6, wherein said chimeric DNA polymerase has
   an E or Q the position corresponding to position 13 of SEQ ID NO:2;
   an I or T at the position corresponding to position 16 of SEQ ID NO:2;
   a T or S at the position corresponding to position 40 of SEQ ID NO:2;
   a G or A at the position corresponding to position 41 of SEQ ID NO:2;
   a V or L at the position corresponding to position 45 of SEQ ID NO:2;
   an L or V at the position corresponding to position 55 of SEQ ID NO:2;
   a Q or D at the position corresponding to position 56 of SEQ ID NO:2;
   a Q or E at the position corresponding to position 61 of SEQ ID NO:2; and
   a K or R at the position corresponding to position 63 of SEQ ID NO:2.

* * * * *

UNITED STATES PATENT AND TRADEMARK OFFICE
CERTIFICATE OF CORRECTION

Page 1 of 1

PATENT NO.        : 9,040,276 B2
APPLICATION NO.   : 11/488535
DATED             : May 26, 2015
INVENTOR(S)       : Michael Borns It is certified that error appears in the above-identified patent and that said Letters Patent is hereby corrected as shown below:

On the title page, item (56), in column 2, References Cited under "Other Publications", line 6, delete "Sicence" and insert -- Science --, therefor.

In the specification
In column 1, line 24, delete "sulfataricus" and insert -- solfataricus --, therefor.
In column 3, line 42, delete "woesii," and insert -- woesei, --, therefor.
In column 6, line 31, delete "domain:" and insert -- domain. --, therefor.
In column 7, line 43, delete "archacabacteria" and insert -- archaebacteria --, therefor.
In column 8, line 32, delete "I6T" and insert -- I16T --, therefor.
In column 10, line 28, delete "woesii," and insert -- woesei, --, therefor.
In column 11, line 30, delete "|560201|" and insert -- |5602011| --, therefor.
In column 12, line 21, delete "pol II" and insert -- pol III --, therefor.
In column 13, line 7, delete "entirety" and insert -- entirety. --, therefor.
In column 16, line 42, delete "Dieffenfach & Dveksler," and insert -- Dieffenbach & Dveksler, --, therefor.
In column 18, line 16, delete ""TCR"" and insert -- "PCR" --, therefor.
In column 21, line 2, delete "archeabacteria" and insert -- archaebacteria --, therefor.
In column 21, line 26, delete "Nonide™" and insert -- Nonidet™ --, therefor.
In column 21, line 41, delete "Trimethlamine" and insert -- Trimethylamine --, therefor.
In column 21, line 48, delete "archael" and insert -- archaea --, therefor.
In column 26, line 4, delete "(Fig. 3)" and insert -- (Fig. 3). --, therefor.

In the claims
In column 53, line 7, in claim 1, delete "Stole" and insert -- Sto7e --, therefor.
In column 53, line 16, in claim 2, delete "Q the" and insert -- Q at the --, therefor.
In column 53, line 38, in claim 3, delete "Stole" and insert -- Sto7e --, therefor.
In column 53, line 47, in claim 4, delete "Q the" and insert -- Q at the --, therefor.
In column 54, line 3, in claim 6, delete "Stole" and insert -- Sto7e --, therefor.
In column 54, line 45, in claim 19, delete "Q the" and insert -- Q at the --, therefor.

Signed and Sealed this
Fifth Day of January, 2016

Michelle K. Lee
*Director of the United States Patent and Trademark Office*